US006878254B2

(12) United States Patent
Yeung et al.

(10) Patent No.: US 6,878,254 B2
(45) Date of Patent: Apr. 12, 2005

(54) SIZE SEPARATION OF ANALYTES USING MONOMERIC SURFACTANTS

(75) Inventors: Edward S. Yeung, Ames, IA (US); Wei Wei, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 431 days.

(21) Appl. No.: 10/085,656

(22) Filed: Feb. 27, 2002

(65) Prior Publication Data

US 2003/0000838 A1 Jan. 2, 2003

Related U.S. Application Data

(60) Provisional application No. 60/273,138, filed on Mar. 2, 2001.

(51) Int. Cl.[7] ..................... G01N 27/447; G01N 27/453
(52) U.S. Cl. ...................... 204/451; 204/455; 204/469; 204/601; 204/605
(58) Field of Search ................................ 204/451, 455, 204/468, 469, 601, 605

(56) References Cited

U.S. PATENT DOCUMENTS 5,290,418 A * 3/1994 Menchen et al. ........... 204/455
5,468,365 A * 11/1995 Menchen et al. ........... 204/455
5,582,705 A * 12/1996 Yeung et al. ............... 204/603

OTHER PUBLICATIONS

Magnusdottir et al, Electrophoresis 1998, 19, pp. 1699–1703.*
Rill et al, J. Chromatography A 817 (1998), pp. 287–295.*
Clothier et al, J. Chromatography A 723 (1996), pp. 179–187.*
Liu et al, ACS Symposium Series (2000), 765, pp. 2–20.*
Rill et al, Chromatographia Supplement I, 49, 1999, pp. S65–S71.*

* cited by examiner

Primary Examiner—Kaj K. Olsen
(74) Attorney, Agent, or Firm—Leydig, Voit & Mayer, Ltd

(57) ABSTRACT

A sieving medium for use in the separation of analytes in a sample containing at least one such analyte comprises a monomeric non-ionic surfactant of the of the general formula, B-A, wherein A is a hydrophilic moiety and B is a hydrophobic moiety, present in a solvent at a concentration forming a self-assembled micelle configuration under selected conditions and having an aggregation number providing an equivalent weight capable of effecting the size separation of the sample solution so as to resolve a target analyte(s) in a solution containing the same, the size separation taking place in a chromatography or electrophoresis separation system.

32 Claims, 16 Drawing Sheets

Time (min)

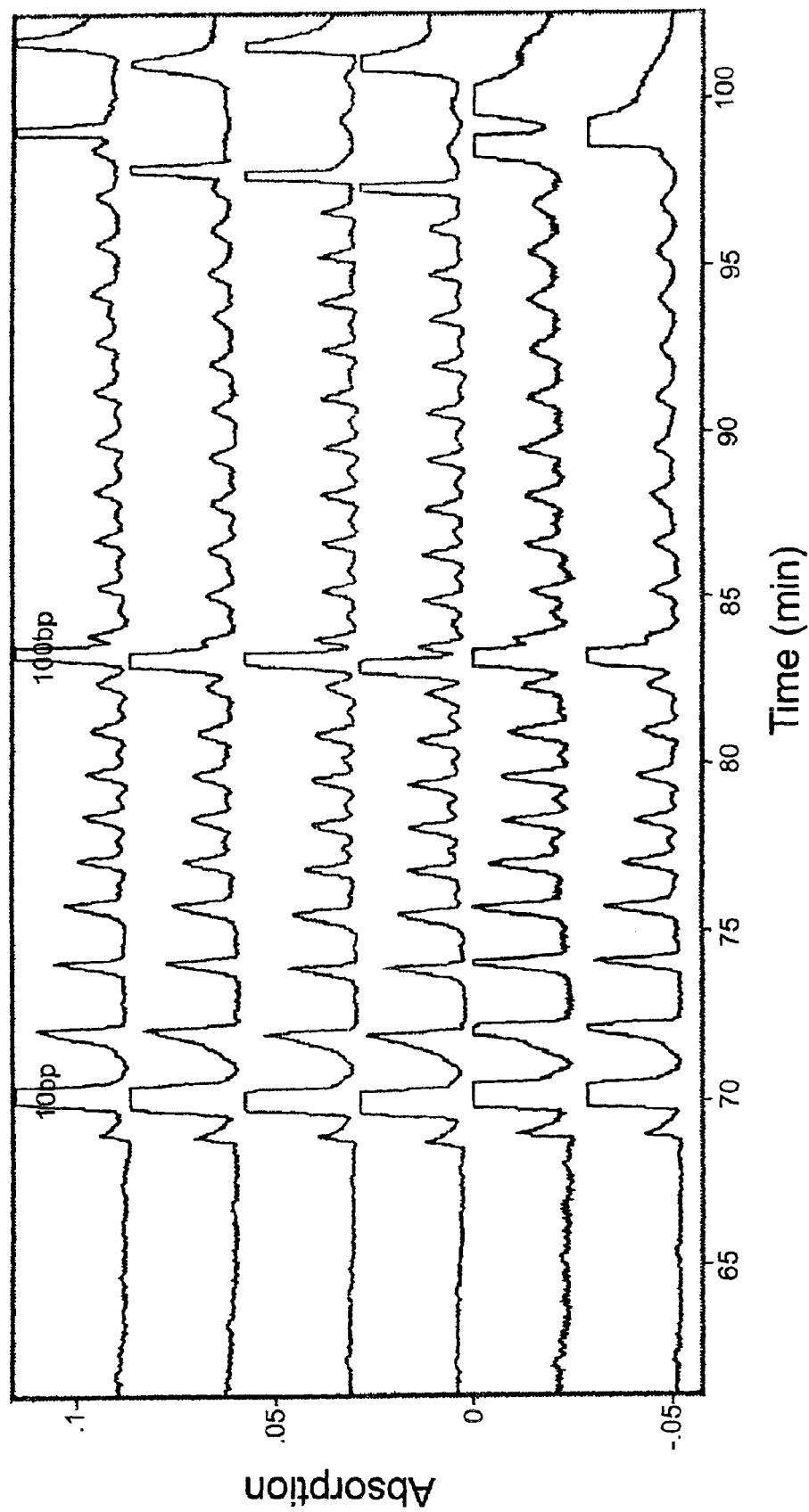

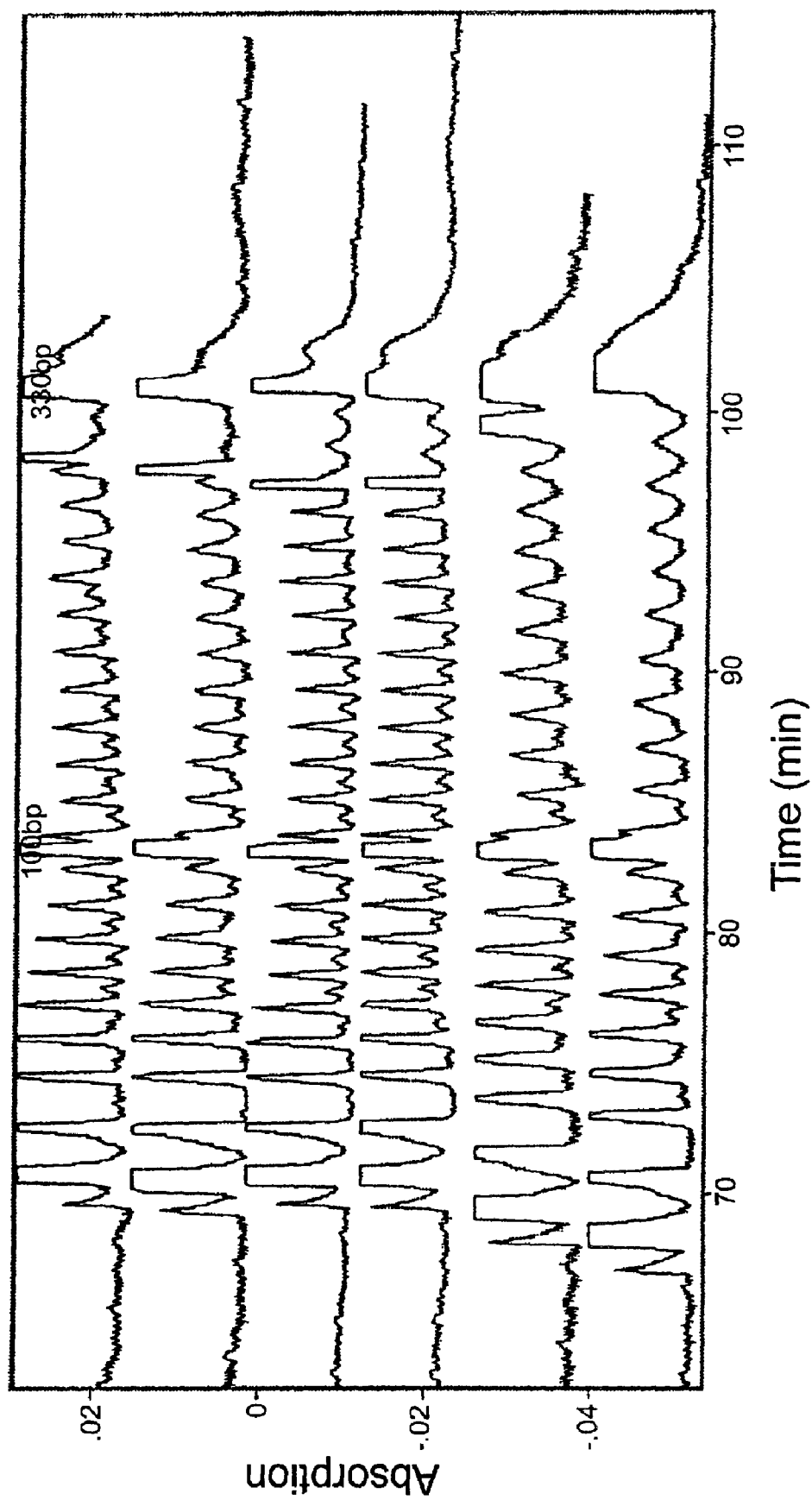

♦ A ■ C ▲ G × T

SIZE SEPARATION OF ANALYTES USING MONOMERIC SURFACTANTS

CROSS-REFERENCE TO RELATED PATENT APPLICATIONS

This patent application claims the benefit of U.S. Provisional Patent Application No. 60/273,138, filed Mar. 2, 2001.

STATEMENT REGARDING FEDERALLY SPONSORED RESEARCH AND DEVELOPMENT

This invention was made, in part, with Government support from the Department of Energy under Grant Number W-7405-ENG-82 and from the National Institutes of Health under Grant Number HG-01804. Therefore, the Government may have certain rights in this invention.

FIELD OF THE INVENTION

This invention pertains to the high speed separation of large molecules (i.e., analytes) based on size in chemical, clinical, pharmaceutical, and other applications.

BACKGROUND OF THE INVENTION

Normally, separation of large molecules (including, for example, DNA) by size in chromatography or in electrophoresis requires use of another large polymer molecule. The most widely used method for separating such large molecules in an electrophoresis system is the use of a gel-sieving matrix.

In recent years, many new gel materials have been described in the scientific literature or disclosed in patents. These materials include polymers made by chemically linking various monomers, or by linking combinations of monomers and cross-linkers, or modified natural polymers.

Non-ionic polymeric surfactants have been used successfully as a separation medium for DNA analysis. These block copolymers have a hydrophobic core of propylene oxide blocks and a strongly hydrated shell of ethylene oxide blocks that can form micelles in solution. The aggregation number is determined by the length of the propylene oxide block. With increasing temperature desolvation of the ethylene oxide groups continues, and the effective volume fraction decreases. These globular micelles overlap and entangle each other at high concentrations. Ultimately, lyotropic liquid crystals are formed that are used as the sieving medium. The spherical micelles that result rely on partitioning based on micellar electrokinetic chromatography or adsorption of the monomers along the DNA chains.

However, these polymers are not always stable due to degradation with time, the testing environment and mechanical shearing during preparation. The separation performance can thus deteriorate due to such degradation.

In addition to degradation over time, the polymeric sieving mediums most commonly employed are relatively difficult to use. Accordingly, for example, filling the capillary tubes used for electrophoresis, and then cleaning such tubes after use, can be, and generally is, relatively difficult. Often, it becomes necessary to replace the capillary tubes due to contamination (stemming from retained sieving medium and/or sample solution).

Also, a polymeric sieving medium cannot be altered. More particularly, the molecular weight of the polymer fixes the application. There is no ability to alter the polymer sieve medium to tailor the medium to different samples having analytes that would optimally require a polymer of a different molecular weight to serve as the sieve medium, i.e., different polymer sieve mediums often will be required for different samples due to the differing composition of the samples.

It would accordingly be highly desirable if it were possible to effect size separation of large molecules using a sieve medium that possessed a relatively low viscosity prior to, and after, size separation so that the sieve medium could be readily put into place, and then easily removed after use. Even further, it would be highly advantageous if a sieving medium could be provided that could be readily tailored to the requirements of a particle sample, so as to allow an efficacious and optimal size separation of the target analyte (s) in such sample.

SUMMARY OF THE INVENTION

The present invention is predicated on the discovery that certain monomeric non-ionic surfactants may be utilized to effect the size separation of large molecules (e.g., DNA samples) while avoiding the disadvantages of previously used sieving mediums. Thus, it has been found that monomeric non-ionic surfactants having a hydrophobic part or end and a hydrophilic part may be advantageously used as sieving mediums in applications ranging from chromatography to electrophoresis to capillary electrophoresis, to effectively carry out the size separation of such large molecules. A particularly useful family of such surfactants are the n-alkyl polyoxyethylene ethers, wherein the n-alkyl chain comprises the hydrophobic end, and the ethylene oxide (EO) groups comprise the hydrophilic end of the molecule. Under appropriate conditions, the hydrophobic (n-alkyl) portion such n-alkyl polyoxyethylene ethers will attract one another to form a sphere-like micelle, wherein the sphere comprises a hydrophobic core comprising the n-alkyl portions of n-alkyl polyoxyethylene ethers, and the outer portion of the sphere comprises the hydrophilic ethylene oxide (EO) groups of said ethers. With the use of an n-alkyl group that is relatively long compared to the length of the EO chain comprising the hydrophilic portion of the molecule, micelles undergo one-dimensional growth by balancing the intermolecular forces. The micellar structures change from sphere to rod-like with such one-dimensional growth. Finally, a giant wormlike micelle forms with huge aggregation numbers. These wormlike or rod-like micelles become sufficiently long and flexible and act as a dynamic polymer solution although they are not chemically linked as in traditional linear polymers.

More generally, the instant invention may be practiced using any monomeric non-ionic surfactant of the general formula B-A, wherein B is a hydrophobic end of the surfactant molecule and A is the hydrophilic end of the molecule. Such molecules balance intermolecular forces and form sphere-like micelles, wherein the core of the spherical micelle comprises the hydrophobic end (B) of said surfactant molecules, and the outer portion of said sphere-like micelles comprises the hydrophilic portions (A) of said surfactant molecules. Under appropriate conditions, such sphere-like micelles aggregate to form long rod-like micelles capable of behaving like a dynamic polymer solution.

The efficacy of utilizing such monomeric surfactants in size separation is substantial. Being soluble in water or other suitable slightly polar organic solvents, a low viscosity solution can be achieved for filling the sieving medium receptacle (e.g., capillary tubes), then heated to an elevated temperature to provide the desired micelle configuration for effecting the size separation, and then the receptacle cleaned by dilution with the solvent after use, as disassembly of the micelle occurs. Accordingly, the sieving medium utilized in this invention is a readily handleable, low viscosity solution, except when in use as the sieving medium during size separation.

Moreover, and importantly, the sieving media of the present invention can be readily altered as desired to tailor the medium for optimal size separation of the molecules in the specific sample involved. More specifically, the equilibrium solution of the self-assembled surfactant micelles resulting from the use of the monomeric non-ionic surfactants results in dynamic long polymer chains that can be tailored to the specific application by adjusting the surfactant concentration in the water or other solvent of use, the separation temperature and buffer additions or denaturants so as to provide the optimal sieve medium.

BRIEF DESCRIPTION OF THE DRAWINGS

FIGS. 10A and B are electropherograms and illustrate the use of standards to provide normalization and align the peaks from the raw data for the various capillaries shown in FIG. 8 and described in Example 7;

DETAILED DESCRIPTION OF THE INVENTION

Figure 1:
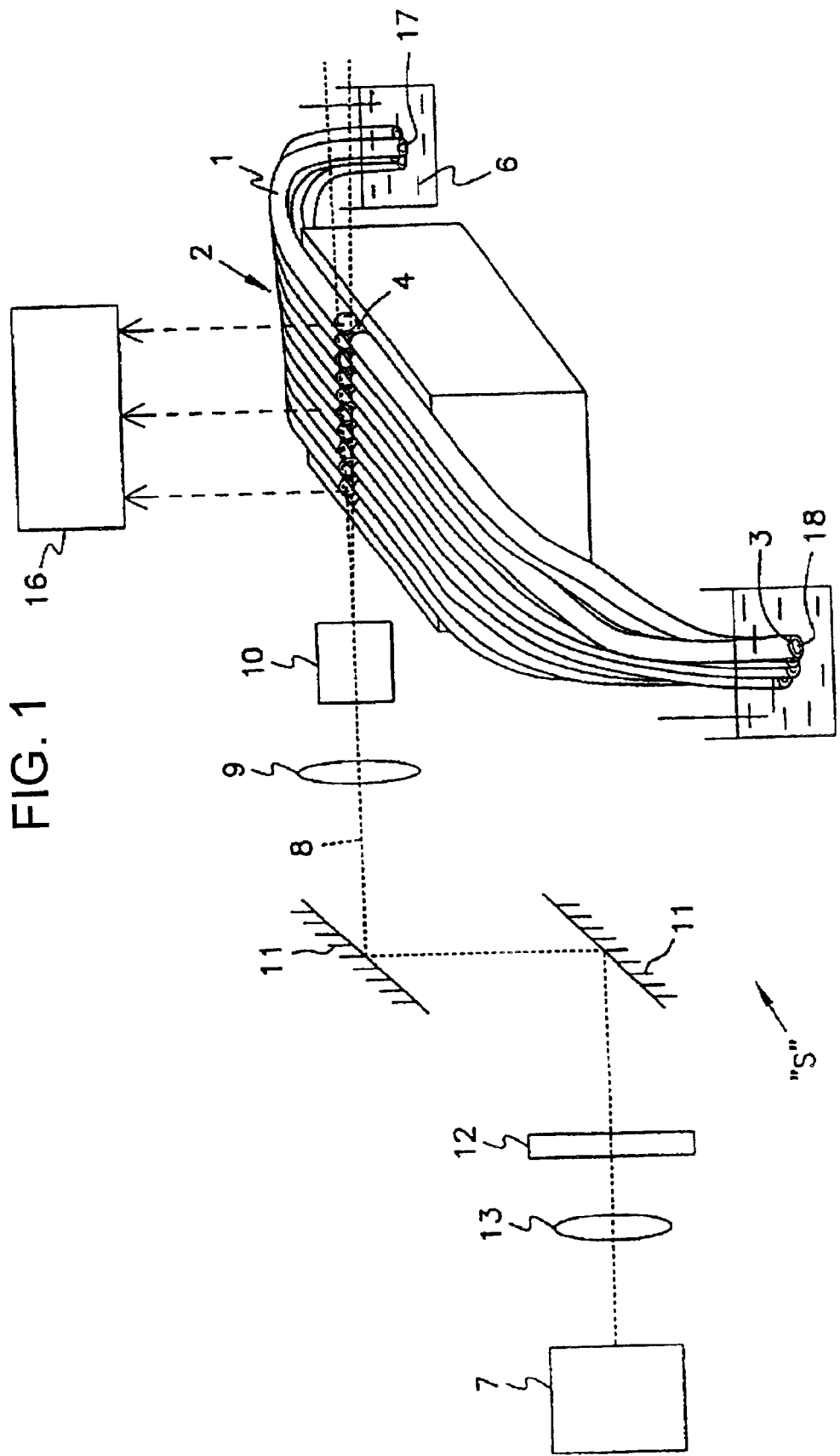
FIG. 1 is a schematic representation of a capillary array electrophoresis system using the non-ionic monomeric surfactants of the present invention.

As stated earlier, it has been found that monomeric non-ionic surfactants having a hydrophobic end and a hydrophilic end, such as the n-alkyl polyoxyethylene ethers, may be advantageously used as sieving mediums in applications ranging from chromatography to electrophoresis to capillary electrophoresis to effectively carry out the size separation of large molecules. More generally, the present invention may be practiced using any monomeric non-ionic surfactants of the formula B-A, wherein B represents the hydrophobic moiety (e.g., n-alkyl), and A represents a hydrophilic moiety (e.g., ethylene oxide). In general, and as has been previously discussed, the present invention can be used for the size separation of analytes of large molecular weight for whatever purpose and may be used in any type of analysis system. Use in a capillary electrophoresis system for the separation of DNA is exemplary. However, this should not be construed so as to limit the application of this invention to use with any other analysis system.

Theoretical Model

In order to understand how surfactant polymer solutions effect DNA separation, we recall the separation mechanism of DNA electrophoresis in traditional polymers. Many theoretical models have been proposed to describe DNA separation in sieving matrices, including Ogston sieving model (see Ogston, A. G. Trans. Faraday Soc. 1958, 54, 1754–1757), reptation (see De Gennes, P. J. J. Chem. Phys. 1971, 55, 572–579), biased reptation model (BRM) (see Slater, G. W.; Kist, T. B. L.; Ren, H.; Drouin, G. Electrophoresis 1998, 19, 1525–1541), constrained release (CR) of entangled polymers (see Duke, T.; Viovy, J. L.; Sememov, A. N. Biopolymers 1994, 34, 239–247, Viovy, J. L.; Duke, T. Electrophoresis 1993, 14, 322–329, Slater, G. W.; Mayer, P.; Hubert, S. J.; Drouin, G. Appl. Theor. Electr. 1994, 4, 71–79, Slater, G. W.; Mayer, P.; Drouin, G. Electrophoresis 1993, 14, 961–966), and "reversible gel" model (see Duke, T.; Viovy, J. L. Phys. Rev. E 1994, 49, 2408–2416). Here, the reversible gel model developed by Duke and Viovy is invoked. In this model, they assumed that the topological constraints on DNA motion in entangled long-chain polymer solutions are perpetually changing as intermolecular bonds break and form or as the polymers diffuse. The mobility of DNA molecules in a temporary gel $\mu$ is, [17]

$$\frac{\mu}{\mu_0} \sim w\tau \sim \left(\frac{c}{c^*}\right)^{-15/4} \frac{\xi}{b} \quad \text{for } w\tau < 1 \tag{1}$$

where $\mu_0$ is the mobility of DNA in free solution, $\xi$ and b are the screening length of the polymer and the Kuhn length of DNA, and c and c* are the solution concentration and entanglement limit, respectively. The separation limit (useful upper limit for size separation) is $$N^* \sim (w\tau)^{-1} \tag{2}$$

where w is the rupture frequency of the cross linking in the temporary gel, such that $$w = 1/\tau_{rep} \tag{3}$$

where $\tau_{rep}$ is the reptation time of the polymer. This model predicates that size fractionation can be extended to higher molecular weight compared to a permanent gel with equivalent pore size.

Static and Dynamic Properties of Entangled Surfactant Micelles

In a micellar system, the reversibility of the self-assembly process ensures that the molecular weight distribution of the worm-like or rod-like polymeric species is in thermal equilibrium, in contrast to traditional long-chain polymer solutions. The static properties of non-ionic surfactants, such as osmotic compressibility, show similar behaviors to those observed in semidilute solutions of long-chain polymers. For worm-like or rod-like micelles, the aggregation number (n) is concentration dependent and can be written as $$n \propto c^\alpha (c > CMC) \quad (4)$$

where CMC is the critical micellar concentration (see Kato, T.; Terao, T.; Tsukada, M.; Seimiya, T. *J. Phys. Chem.* 1993, 97, 3910–3917). The value of $\alpha$ depends on the model for association equilibrium, and is typically equal to 0.5. The contour length of n-monomers, $L_n$, can be described as, $$L_n = \frac{nv_c}{\pi l_c^2} + \frac{2l_c}{3} + 2l_h \quad (5)$$

where $v_c$ and $l_c$ are the volume and minor radius of the micelle core of the surfactant hydrophobic moiety, respectively, and $l_h$ is the effective length of the surfactant hydrophilic moiety (see Carale, T.; Blankschtein, D. *J. Phys. Chem.* 1992, 96, 459–467). The radius of gyration of n-monomers is given as,[36]

$$\langle R_g^2 \rangle = \frac{L_n \xi_m}{3} - \xi_m^2 + \frac{2\xi_m^3}{L_n} - \frac{2\xi_m^4}{L_n^2}\left[1 - \exp\left(-\frac{L_n}{\xi_m}\right)\right] \quad (6)$$

For $\xi_m \gg L_n$ $$\langle R_g^2 \rangle \approx \frac{L_n^2}{12} \quad (6a)$$

and for $\xi_m \ll L_n$ $$\langle R_g^2 \rangle \approx \frac{L_n \xi_m}{3} \quad (6b)$$

where $\xi_m$ is the persistence length of the micelle (i.e., the finite diameter of the micelle) which results from steric interactions between the hydrophilic moiety at the micelle core/water interface (see Carale, T.; Blankschtein, D. *J. Phys. Chem.* 1992, 96, 459–467). When the surfactant concentration is above the crossover point from dilute to semidilute solution regimes, the monomers entangle each other and form a transient network of overlapping micelles (see Cates, M. E.; Candau, S. J. *J. Phys.: Condens. Matter* 1990, 2, 6869–6892, Kato, T.; Terao, T.; Tsukada, M.; Seimiya, T. *J. Phys. Chem.* 1993, 97, 3910–3917, Carale, T.; Blankschtein, D. *J. Phys. Chem.* 1992, 96, 459–467).

According to scaling law, the corrected length of the micelles ($\xi_b$), which is similar to the gel pore size, is $$\xi_b = (R^*_g/\sqrt{3})(c/c^*)^{\nu/(1-3\nu)} \quad (7)$$

where $c^*$ is crossover concentration, $R^*_g$ is the radius of gyration at the crossover concentration and $\nu$ is a constant in the range of 0.5 to 0.588 (see Kato, T.; Terao, T.; Tsukada, M.; Seimiya, T. *J. Phys. Chem.* 1993, 97, 3910–3917).

From Eqs. 4 to 7, the static properties (effective molecular weight, radius of gyration, etc.) of the transient network of overlapping micelles are determined by surfactant concentration and physical structure (hydrophilic and hydrophobic moieties), which are therefore different from those governing traditional long-chain polymers. The dynamic properties of self-assembled micelles (viscoelasticity, self-diffusion, etc.) are also distinguishable from entangled long-chain polymers (see Cates, M. E.; Candau, S. J. *J. Phys. Condens. Matter* 1990, 2, 6869–6892, Cates, M. E. *J. Phys.: Condens. Matter* 1996, 8, 9167–9176, Kato, T.; Terao, T.; Tsukada, M.; Seimiya, T. *J. Phys. Chem.* 1993, 97, 3910–3917). The flexible worm-like micelles behave like dynamic polymers, whose chains are subject to reversible breakage and formation. The dynamic properties of such polymers in the entangled state can be described by a modified reptation model, in which the scission and recombination reactions of the chains are introduced. The lifetime of a chain with mean length ($\bar{L}$) before breaking into two pieces ($\tau_b$) is defined as, $$\tau_b = 1/k\bar{L} \quad (8)$$

where the mean length ($\bar{L}$) can be expressed as, $$\bar{L} \cong \phi^{1/2} \exp\left(\frac{E_C}{2k_B T}\right) \quad (9)$$

and $E_c$, the end-cap energy (in units of $k_B T$), is the difference in the free energy of adding surfactant molecules to the worm-like core versus adding molecules to the two spherical end-caps of the micelle (see Cates, M. E.; Candau, S. J. *J. Phys.: Condens. Matter* 1990, 2, 6869–6892, Cates, M. E. *Macromolecules* 1987, 20, 2289–2296, Groswasser, A. B.; Wachtel, E.; Talmom, Y. *Langmuir* 2000, 16, 4131–4140). $E_c$ is independent of concentration and is linearly dependent on temperature. $\phi$ is the total volume fraction of the surfactant defined as $$\phi = \sum L_n c(L_n) \propto \sum L_n \exp\left(-\frac{L_n}{\bar{L}}\right) \quad (10)$$

where $c(L_n)$ is the number density of chains of length $L_n$.

When the lifetime is long ($\tau_b \gg \tau_{rep}$), the dynamic polymer is like traditional unbroken polymers. However, for short lifetimes ($\tau_b \ll \tau_{rep}$), the stress relaxation time scale ($\tau$) is given by $$\tau = (\tau_{rep} \tau_b)^{1/2} \quad (11)$$

where $\tau_{rep}$ is relaxation time of chains disentangled from a tube-like environment, i.e., the reptation time, $$\tau_{rep} \cong \frac{\bar{L}^2}{D_c} \quad (12)$$

and $D_c$ is the collective diffusion constant, which is related to the hydrodynamic correlation length ($\xi_H$), $$D_c = \frac{k_B T}{6\pi \eta_s \xi_H} \propto c^x \quad (13)$$

$\xi_H$ scales like $\xi_b$, in semidilute regime and decreases with the increase of surfactant concentration. x is a constant. In the low concentration regime, $x = -5/3$ (see Cates, M. E.; Candau, S. J. *J. Phys.: Condens. Matter* 1990, 2, 6869–6892), and in the high concentrated regime, $x = 2/3$ (see Kato, T.; Terao, T.; Tsukada, M.; Seimiya, T. *J. Phys. Chem.*

1993, 97, 3910–3917, Kato, T.; Terao, T.; Seimiya, T. *Langmuir* 1994, 10, 4468–4474). Thus, $D_c$ first decreases with increasing concentration and then increases.

Separation Limit in Dynamic Polymers

By combining Eqs. 2–3 and 8–12, the mobility of DNA molecules in dynamic polymers is obtained, $$\frac{\mu}{\mu_0} \sim \frac{D_c^{\frac{1}{2}}}{\bar{L}^{\frac{3}{2}}} \tag{14}$$

as well as the separation limit, $$N^* \sim \frac{\bar{L}^{3/2}}{D_c^{1/2}} \tag{15}$$

The present results are different from traditional long-chain polymer solutions. In order to achieve long reads, a large $\bar{L}$ and a small $D_c$ are preferred. $\bar{L}$, from Eq. 9, is determined by the temperature and the total volume fraction (surfactant concentration). Higher temperatures and concentrations give rise to large $\bar{L}$ (see Balmbra, R. R.; Clunie, J. S.; Corkill, J. M.; Goodman, J. F. *Trans. Faraday Soc.* 1964, 60, 979–985, Cates, M. E.; Candau, S. J. *J. Phys.: Condens. Matter* 1990, 2, 6869–6892, Groswasser, A. B.; Wachtel, E.; Talmom, Y. *Langmuir* 2000, 16, 4131–4140). However, $D_c$ shows a different concentration dependence. In the low concentration regime, $D_c$ decreases with increasing concentration (Eq. 13). Thus, long reads should be obtained by increasing the surfactant concentration. At the high concentration regime, $\bar{L}$ increases with concentration as $\phi^{1/2}$ while $D_c$ also increases with concentration as $\phi^{2/3}$. Thus, $N^* \sim \phi^{5/12}$ according to Eq. 15 and increasing the concentration is worse for long reads. In addition, it is noted that $M_w \sim \bar{L}$. At a given set of conditions, it is preferred to use surfactants with a large aggregation number (large $M_w$) to achieve a large $\bar{L}$.

Suitable Monomeric Non-Ionic Surfactants

As regards suitable monomeric non-ionic surfactants, those of the n-alkyl polyoxyethylene ether family, wherein the n-alkyl chain comprises a hydrophobic end of the molecule and the ethylene oxide (EO) groups comprise a hydrophilic end of the molecule, may be used. However, the present invention may be practiced using any monomeric non-ionic surfactant of the formula B-A, wherein B represents a hydrophobic moiety and A represents a hydrophilic moiety. More particularly, the surfactants selected are preferably completely soluble in the water or a suitable slightly polar organic solvent (e.g., dimethylformamide, tetrahydrofuran, methylethylketone) at a concentration, and under conditions, which will provide the apparent equivalent weight of the self-assembled micelle in solution required for the particular application. To achieve the relatively high aggregation numbers required, the hydrophilic moieties, A, should be susceptible to hydrogen bonding or the like so as to provide the desired worm-like micelles. Most preferably, the surfactants utilized should have relatively large aggregation numbers, which can be considered as the equivalent weight, while having a relatively low critical micellar concentration (CMC). Thus, surfactants having an aggregation number of at least 100 are preferred, even more preferably at least 1,000. The static properties (effective molecular weight, radius of gyration, and the like) of the self-assembled, transient network of the overlapping micelles that form the worm-like structure are determined by the surfactant concentration and the physical structure of the surfactant (viz., the hydrophilic and hydrophobic moieties).

Suitable specific examples of satisfactory monomeric non-ionic surfactants of this invention are the n-alkyl polyoxyethylene ethers in which the length of the carbon chain ("C"), the hydrophobic portion of the molecule, is 14 to 16 carbon atoms, and the EO groups comprising the hydrophilic portion of the molecule number 6 to 8. Most preferably, useful surfactants comprise $C_{16}E_6$, $C_{16}E_8$, and $C_{14}E_6$ wherein E represents the EO hydrophilic moieties.

Hydrophobic backbones other than n-alkyl chains can be employed. Chains including vinyl groups or the like thus can also be used.

Separation Systems

Separation systems for which the present invention can be used to separate analytes (i.e. molecules) are characterized by the method of separation used. In electrophoresis, for example, analytes with a net charge are separated by an electrical current, which causes analytes to migrate in a particular direction of the current. In chromatography, separation is carried out by the use of pressure caused by liquid, gas, or any other medium that pressures analytes to move toward a particular direction. Generally speaking, such separations take place in a particular separation system within a receptacle such as a tube (metal or plastic), microfabricated channels, or capillaries, that contains a particular sieving medium. The receptacles in which the present invention are used preferably have an inlet (intake end) and an outlet (outflow end), wherein the sample to be analyzed is introduced into the intake end of the receptacle and, due to migration caused by electrophoresis or chromatography, migrates toward the outflow end of the receptacle.

With respect to electrophoresis systems used in the analysis of genetic material, the medium in which separation traditionally took place was slab gel (see G. L. Trainor, *Anal. Chem.*, 62, 418–426 (1990)). Recently, capillary electrophoresis (CE) has emerged as a powerful separations technique, with applicability toward a wide range of molecules from simple atomic ions to large DNA fragments. In particular, capillary gel electrophoresis (CGE) has become an attractive alternative to slab gel electrophoresis (SGE) for biomolecule analysis, including DNA sequencing. See, for example, Y. Baba et al., *Trends in Anal. Chem.*, 11, 280–287 (1992). This is generally because the small size of the capillary greatly reduces Joule heating associated with the applied electrical potential. Furthermore, CGE produces faster and better resolution than slab gels.

More particularly, in capillary electrophoresis, DNA usually migrates against electroosmotic flow (EOF). Coated capillaries or buffer additives are often used for reducing EOF. Non-ionic surfactants, such as Brij 35 ($C_{12}E_{23}$), have been employed for decreasing EOF in CE (see Towns, J. K.; Regnier, F. E. *Anal. Chem.* 1991, 63, 1126–1132, Salmanowicz, B. P. *Chromatographia* 1995, 41, 99–106, Durkin, D.; Foley, J. P. *Electrophoresis* 2000, 21, 1997–2009). Ellipsometry studies also confirmed that non-ionic surfactants are easily absorbed onto the polar or hydrophilic silica/water interface to form a constant thickness layer (see Tiberg, F.; Jonsson, B.; Lindman, B. *Langmuir* 1994, 10, 3714–3722). In fact, because the monomers are small compared to other DNA sieving matrices typically used, the coating resulting from the present invention is expected to be more uniform and more easy to put on and to wash off. Thus, a bare capillary may be used.

N-alkyl polyoxyethylene ethers ($C_{16}E_6$, and $C_{16}E_8$) have low CMC and large aggregation numbers (see Becher, P. *Nonionic Surfactants: Physical Chemistry*; Marcel Dekker: New York, 1967, Schick, M. J. *Nonionic Surfactants: Physical Chemistry*; Marcel Dekker: New York, 1986, Balmbra, R. R.; Clunie, J. S.; Corkill, J. M.; Goodman, J. F. *Trans. Faraday Soc.* 1964, 60, 979–985, Cummins, P. G.; Staples, E. *Langmuir* 1989, 5, 1195–1199, Lin, Z.; Scriven, L. E.; Davis, H. T. *Langmuir* 1992, 8, 2200–2205). For instance, the CMC of $C_{16}E_6$ is 1 $\mu$M (see Becher, P. *Nonionic Surfactants: Physical Chemistry*; Marcel Dekker: New York, 1967) and the apparent micelle length for 1% $C_{16}E_6$ at 28° C. is 340 nm, which is comparable to the length of 1 kb ds-DNA. When the temperature increases to 38° C., the micelle length reaches 700 nm (see Cummins, P. G.; Staples, E. *Langmuir* 1989, 5, 1195–1199, Lin, Z.; Scriven, L. E.; Davis, H. T. *Langmuir* 1992, 8, 2200–2205). The size of the micelles can be adjusted by changing both the surfactant concentration and the temperature (see Balmbra, R. R.; Clunie, J. S.; Corkill, J. M.; Goodman, J. F. *Trans. Faraday Soc.* 1964, 60, 979–985, Groswasser, A. B.; Wachtel, E.; Talmom, Y. *Langmuir* 2000, 16, 4131–4140). Moreover, the micelle size is determined by the structure of the surfactants. At the same concentration and temperature, the aggregation number of $C_{16}E_6$ is larger than that of $C_{16}E_8$. Therefore, the desirable dynamic polymer size can be easily controlled.

In general, the instant invention may be used within any separation receptacle in any separation system. In a preferred embodiment, an electrophoresis system using multiplexed capillaries for separation is used. An example of such suitable system is described in Gao, Q.; Pang, H. -M.; Yeung, E. S., *Electrophoresis*, 20, pp. 1518–1526 (1999). Other suitable capillary array electrophoresis systems are described in U.S. Pat. Nos. 5,324,421, 5,498,324, 5,582,705, 5,695,626, and 5,741,411 to Yeung et al. The disclosures of the instrumentation shown, and the protocols described, in these patents are incorporated herein by reference.

The sieving medium can be loaded into the receptacle for the particular separation technique by any means desired, many techniques being known and useful. Thus, for example, in the case of capillary electrophoresis, the sieving media employed in the present invention can be injected using pressure, as often employed with the relatively viscous polymeric mediums previously used. This technique will be most useful when the monomeric surfactants of this invention are assembled into the desired micellar configuration prior to loading.

However, the monomeric surfactants used in this invention are relatively low viscous solutions at ambient temperatures, and at the concentration that generally will be used (i.e., ranging from perhaps as low as 0.1% up to 10% or more, depending upon the requirements of the particular application. Accordingly, and, pursuant to the present invention, the non-ionic monomeric surfactant used is first formed into a solution with the solvent and concentration desired, with a buffer or the like being added as considered appropriate. Then, the thus formed solution can be injected into the capillaries as a low viscosity solution. Increasing the temperature to the run temperature desired will then allow the more viscous and desired micellar structure to be self-assembled. Following completion of the run, and allowing the temperature to come to ambient, the low viscosity solution that returns can be easily removed, as by injecting an appropriate acid (e.g., HCl) and then rinsing with deionized water or the like.

Further, and as may be appreciated from the Examples which follow, the present invention is not only capable of being used in a relatively facile manner, but is highly versatile. Thus, previously used polymeric gel sieving mediums were somewhat limited. Once the polymer molecular weight that was most suitable for a particular use was selected, that circumscribed the utility. The molecular weight of the polymer could not be altered.

In direct contrast, and in accordance with a further aspect of this invention, the micellar configuration that is assembled cannot only be readily disassembled, but can thereafter be further reassembled, as desired. Accordingly, by utilizing the same surfactant, the characteristics of the micellar configuration can be adjusted by varying the concentration and use temperature so as to tailor the sieving machines to the parameters required for the particular sample or analyte(s) of interest.

Figure 2A:
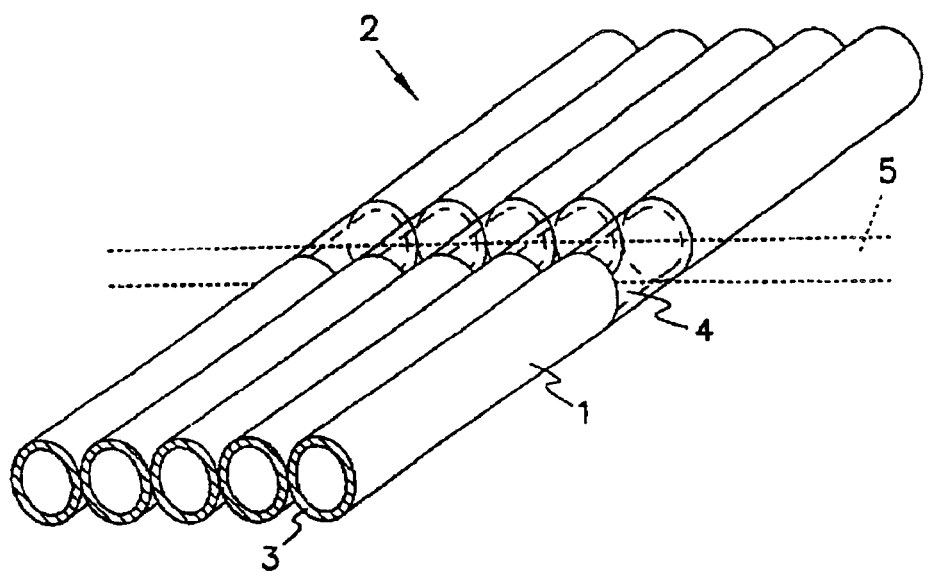
FIGS. 2A and 2B show a more detailed representation of the individual capillaries depicted in the system.

FIGS. 1 and 2 show one suitable capillary array electrophoresis system according to the present invention. Capillaries 1 are arranged in a coplanar, parallel array 2. The annular wall 3 of each capillary 1 has a first transparent portion 4. The transparent portion 4 is transparent to light having a wavelength about equal to a wavelength of a beam of coherent light used to irradiate a target species in a capillary. Each capillary is loaded with a non-ionic monomeric surfactant of the present invention at the concentration and use temperature selected to provide the appropriate micelle for the target analyte(s) in the sample(s) to be analyzed. Together, the transparent portions 4 of the annular walls 3 define a transparent path 5 extending through the capillary array 2 perpendicular to the capillaries 1, as best seen in FIG. 2A.

Side-entry irradiation of target species (a technique more thoroughly described in U.S. Pat. No. 5,741,411) in a capillary 1 is effected through the transparent portion 4 of the annular wall 3 of each capillary 1 in the array 2, as shown in FIG. 1. Light passes through the transparent portion 4 of each capillary 1 in the array 2 in a sequential manner. A coherent light source 7 is positioned to direct a beam 8 of coherent light along the transparent path 5 (see FIGS. 2 and B). The beam 8 of coherent light in FIG. 1 can be focused and collimated through a collimating focusing lens 9 interposed between the coherent light source 7 and the capillary array 2. The focused line of the laser may be altered with a beam expander 10 in order to more effectively irradiate a large number of capillaries. The beam 8 can optionally be altered or redirected, as with a mirror 11, filter 12 or lens 13, prior to contacting the array 2

Figure 2B:
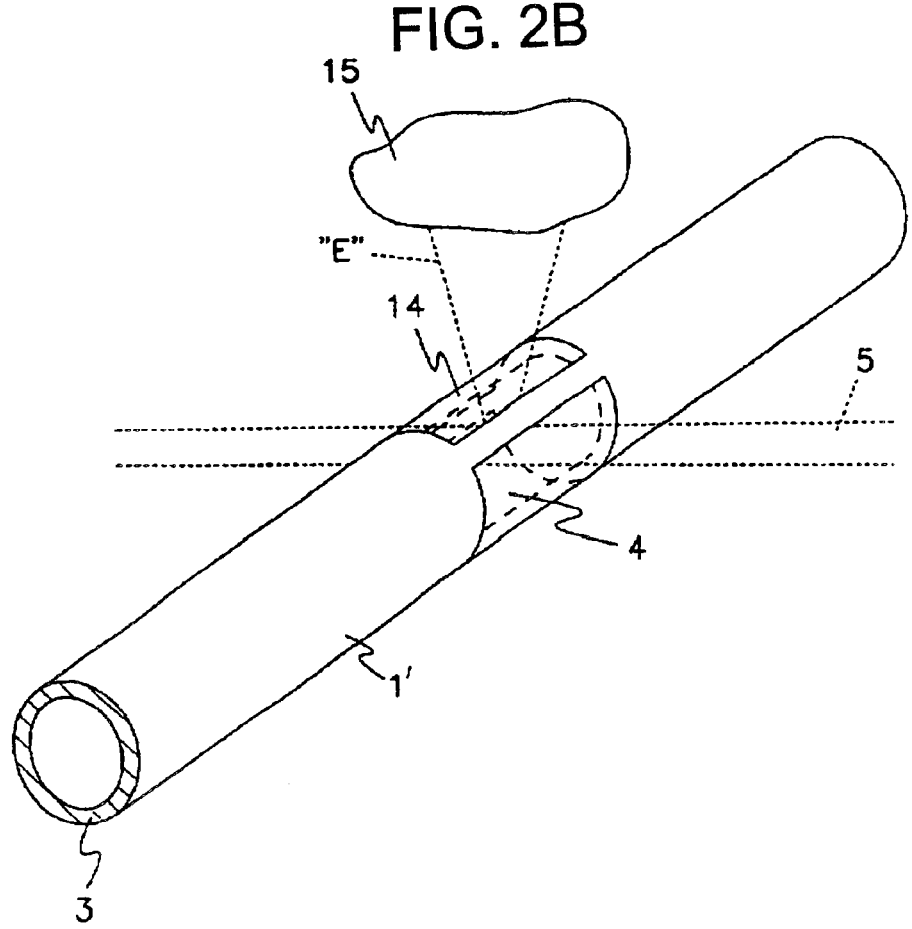

FIGS. 2A and 2B show an alternative embodiment of the system "S" wherein the annular walls 3 of the capillaries 1' have a second transparent portion 14 for optically coupling the transparent path 5 to a location 15 external to the capillary array, such that electromagnetic radiation can travel between the two sites. The location 15 external to the capillary array preferably contains an optical detector 16.

As shown in FIG. 1, at least one capillary 1 may be in fluid communication with a sample 6 so that the sample 6 is drawn into the capillary 1. Each capillary has an intake end 17, an outflow end 18, and an annular wall 3 with a first transparent portion 4 defining a transparent path 5 extending through the capillary array 2 perpendicular to the capillaries 1. Where detection is to take place via laser-induced fluorescence, a sample containing a fluorescent target species is introduced into the intake end 17 of at least one capillary 1 such that the sample migrates through the capillary 1 toward the outflow end 18. Preferably, sample introduction is accomplished using pressure injection as disclosed in more detail in U.S. Pat. No. 5,741,411. Fluorescence emission may be induced from the target species by irradiating it with a beam of coherent light 8 directed along the transparent path 5 (see FIG. 2A).

Where a capillary contains fluorescing target species, fluorescence detection can also be effected by any convenient alternative means, as by using optical fibers. Optical fibers can, for example, be optically coupled to the transparent path 5 axially by inserting one or more optical fiber into a capillary (Yeung et al., U.S. Pat. No. 5,324,401, Jun. 28, 1994, incorporated herein by reference).

Figure 3:
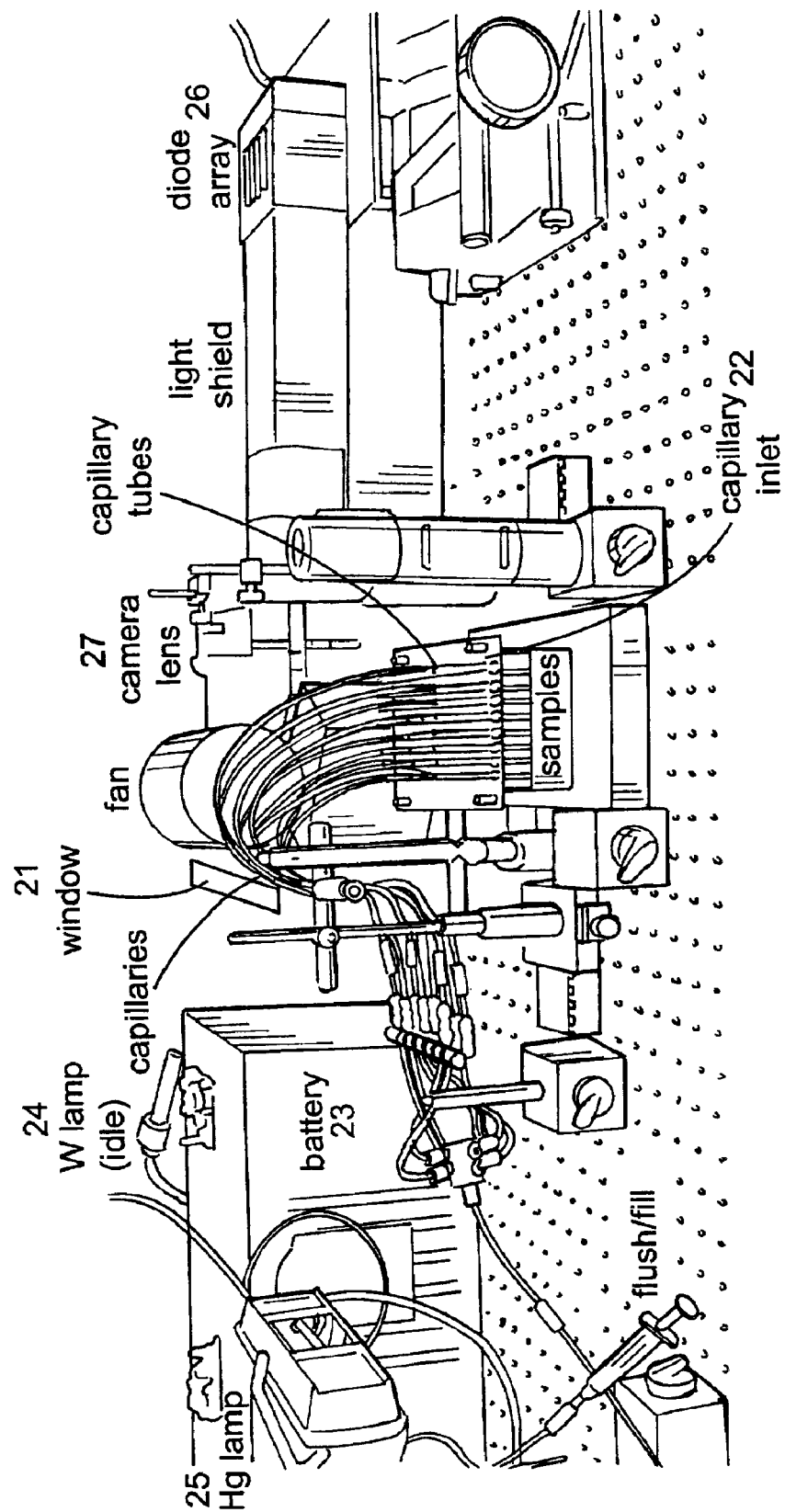
FIG. 3 is a schematic representation of a capillary electrophoresis system utilizing UV/absorption-based detection in which the present invention may be used.

The instant invention may also be used in a capillary electrophoresis separation system utilizing UV/absorption-based detection. FIG. 3 shows one such embodiment. Capillaries are packed side-by-side at the detection window 21 (FIG. 3). At the outlet of the capillary array, the capillaries are bundled together to allow simultaneous buffer filling and rinsing. At the injection end (inlet), the capillary array is spread out and mounted on a copper plate to form a format with dimensions that fit into a microtiter plate for sample introduction as indicated at 22. The sieving medium comprising non-ionic monomeric surfactants is introduced into the inlet of the capillaries, suitably by pressure injection as disclosed in U.S. Pat. No. 5,741,411. In addition, conductive pins are located next to the capillary tips to serve as individual electrodes. Sample and buffer trays are moved and aligned under the capillary inlets, so that the capillary array is never physically moved. A high voltage DC power supply 23 provides power for the electrophoresis, with all the electrodes being connected to the same power supply.

In the system illustrated in FIG. 3, the light source, filter, capillary array holder, camera lens, and detector are all contained in a light-tight metal box attached to an optical table. The light source may be an AC or DC light source, and may be single wavelength or multiple wavelengths. In FIG. 3, a tungsten lamp 24 or a hand-held mercury lamp 25 is used for visible or UV detection, respectively. Generally, the light source, the capillary array, and the optical detector (the photodiode array detector 26) are aligned in a linear manner, as generally described in U.S. Pat. No. 5,900,934 (Gilby et al.), and shown in FIG. 3. The system comprises an optical detector capable of detecting transmission of light through a sample in a capillary. The optical detector is preferably a photodetector array that includes a plurality of photosensitive elements providing a serial output. The elements are preferably pixels of a photodiode array, wherein the detector has linear aligned pixels located in a plane parallel to the capillary array. The photodiode array detector 26 is optically coupled to the capillary array such that at least one of the capillaries in the capillary array is optically coupled to less than about ten of the linearly aligned pixels. An imaging lens 27 may optionally be interposed between the capillary array and the image detector used to optically couple the pixels to the capillaries. Further, an interference filter may be employed to filter light transmitted from the capillary array in order to define the absorption wavelength.

In the UV/absorption-based multiplexed capillary electrophoresis system illustrated in FIG. 3, the annular wall of each capillary in the array contains a transparent portion for use in optically coupling the interior portion of the capillary to the photodiode array detector. A sample containing any absorbing target species (e.g. DNA) is introduced into the inlet of the capillary such that it migrates through the capillary containing the sieving medium of the present invention toward the capillary outlet. Absorption by the target species is then induced by irradiating it with a beam of light from the light source. The level of absorbance is detected by the photodiode array detector through the transparent portion of the optically coupled capillary using the optically coupled pixels.

A more complete description of an embodiment of a multiplexed capillary electrophoresis system utilizing UV/absorption based detection for which the present invention may be used may be found in U.S. Provisional Application 06/153,263 and PCT/US00/20447, and those references are hereby incorporated in there entirety.

The following Examples further illustrate the invention but, of course, should not be construed as in any way limiting its scope.

Examples 1–5 utilize the present invention in a multiplexed capillary electrophoresis system employing fluorescence-based detection, employing the following Instrumentation and Chemicals and Materials.

Instrumentation

CE instrument with laser-induced fluorescence (LIF) detection, built in-house, has been described in previous work (see Wei, W.; Yeung, E. S. *J. Chromatogr. A* 2000, 745, 221–230). Briefly, about 10-mW of 488-nm laser light from an argon-ion laser (Model Innova 90, Coherent, Palo Alto, Calif.) was used for excitation. The laser beam was focused on the detection region of the capillary by a 1-cm focal length lens at an angle of 90° to the laser beam. A 530-nm long-pass filter was used to eliminate the scattered light before imaging onto the photomultiplier tube (PMT). The fluorescence signal from the PMT was transferred directly through a 10-kΩ resistor to a 24-bit A/D converter (Lawson Labs, Kalispell, Mont.) and stored in a 486/33 computer at 4 Hz.

Fused-silica capillaries with 50-$\mu$m I.D. and 363-$\mu$m O.D. were purchased from Polymicro Technologies (Phoenix, Ariz.). The separation capillary was enclosed in a 0.5-cm I.D. copper heating jacket. The jacket is connected to a water bath circulator (Fisher Scientific). A model HH23 microprocessor thermometer was directly connected to the outside of the copper tube so that the separation temperature can be directly read with a precision of 0.1° C.

Chemicals and Materials

All chemicals were obtained from Sigma (St. Louis, Mo.). The buffer for ds-DNA fragments analysis is composed of 100 mM combined HEPES and triethylamine (TEA) at pH 7.0. For DNA sequencing, the buffer consists of 75 mM 3-[[tris(hydroxymethyl)-methyl]propanesulfonic acid (TAPS), 75 mM histidine, 50 mM tris(hydroxymethyl) aminomethane (Tris) and 2 mM EDTA with 7 M urea. 10-bp, 25-bp, 1-kb and 5-kb DNA ladders from Life Technologies (Frederick, Md.). 6-FAM labeled 100-bp size standard was from Transgenomics (Omaha, Nebr.). The intercalated dyes for DNA labeling (1:5 dye:DNA), Thiazole orange (TO) and SYBR® Gold nucleic acid stain, were from Molecular Probes (Eugene, Oreg.). M13(-21) DNA samples were prepared at the Nucleic Acid Facility (Iowa State University, Ames, Iowa) by using cycle sequencing, BigDye-primer, Ampli Taq FS polymerase and standard Applied Biosystems reagents. The DNA samples were denatured by heating in a denaturing solution [1:1 (v/v) formamide/saturated urea] at 95° C. for 3 min and then put onto ice for 3 min.

EXAMPLE 1

Figure 4:
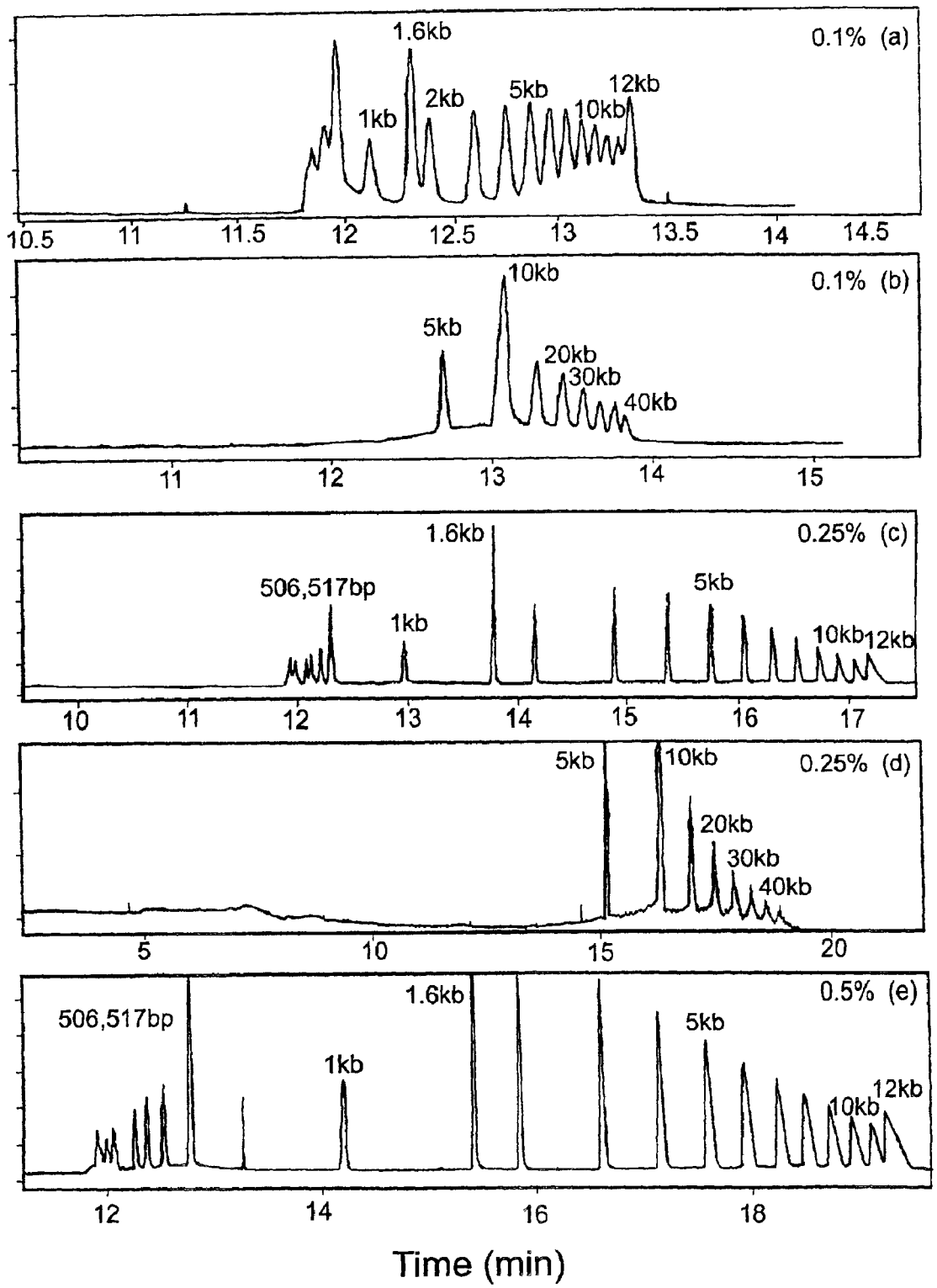
FIG. 4 are electropherograms, labeled (a)–(e), illustrating resolution of two DNA markers (a 1-kb and a 5-kb ladder) in samples at various surfactant concentrations.

This Example illustrates the role of surfactant concentration on separation performance. In a first set of test runs, samples containing 1-kb and 5-kb DNA ladders as markers were separated at different $C_{16}E_6$ concentrations using the Instrumentation previously described. Sample introduction, as well as the surfactant introduction prior to the sample introduction, was accomplished by pressure injection as disclosed in U.S. Pat. No. 5,741,411. FIG. 4 shows the concentration dependence on the separation limit (conditions: $L_{eff}$=60 cm, E=250 V/cm, 1 $\mu$M TO in 100 mM HEPES-TEA buffer (pH 7.0), room temperature). In the FIG. 3 electropherograms labeled (a) and (b), the resolution for the 1-kb and 5-kb DNA ladders is poor at 0.1% of $C_{16}E_6$. When the concentration increases to 0.25%, both 1-kb and 5-kb ladders can be resolved well (see FIG. 4 *c* and *d*).

According to Eq. 15, when the concentration increases in the low concentration regime, $\overline{L}$ increases and $D_c$ decreases such that the separation limit is extended. Therefore, at these conditions, 0.25% separates the low from the high concentration regimes. However, when the surfactant concentration was increased further (up to 0.5%), for the 1-kb ladder improved resolution was not observed, as shown in FIG. 4e. On the other hand, the resolution for large DNA is decreased, which results from the increase of $D_c$ with concentration. In FIG. 4c through e, the larger fragments show asymmetric peaks characteristic of mismatch between their mobilities and those of the buffer ions usually observed only in zone electrophoresis (see Mikkers, F. E. P.; Everaerts, F. M.; Verheggen, T. P. E. M. *J. Chromatogr.* 1979, 169, 11–20).

EXAMPLE 2

This Example further illustrates the effect of surfactant concentration on separation of DNA samples.

A set of test runs was conducted using samples containing a 6-FAM labeled 100-bp DNA ladder as a marker, with each test run attempting to resolve the 100-bp ladder under different concentrations of $C_{16}E_6$ (conditions: $L_{eff}$=30 cm, 100 mM HEPES-TEA buffer (pH 7.0) with 6 M urea, E=250 V/cm). Again, sample introduction, as well as the surfactant introduction prior to the sample introduction, was accomplished by pressure injection as disclosed in U.S. Pat. No. 5,741,411.

Figure 5:
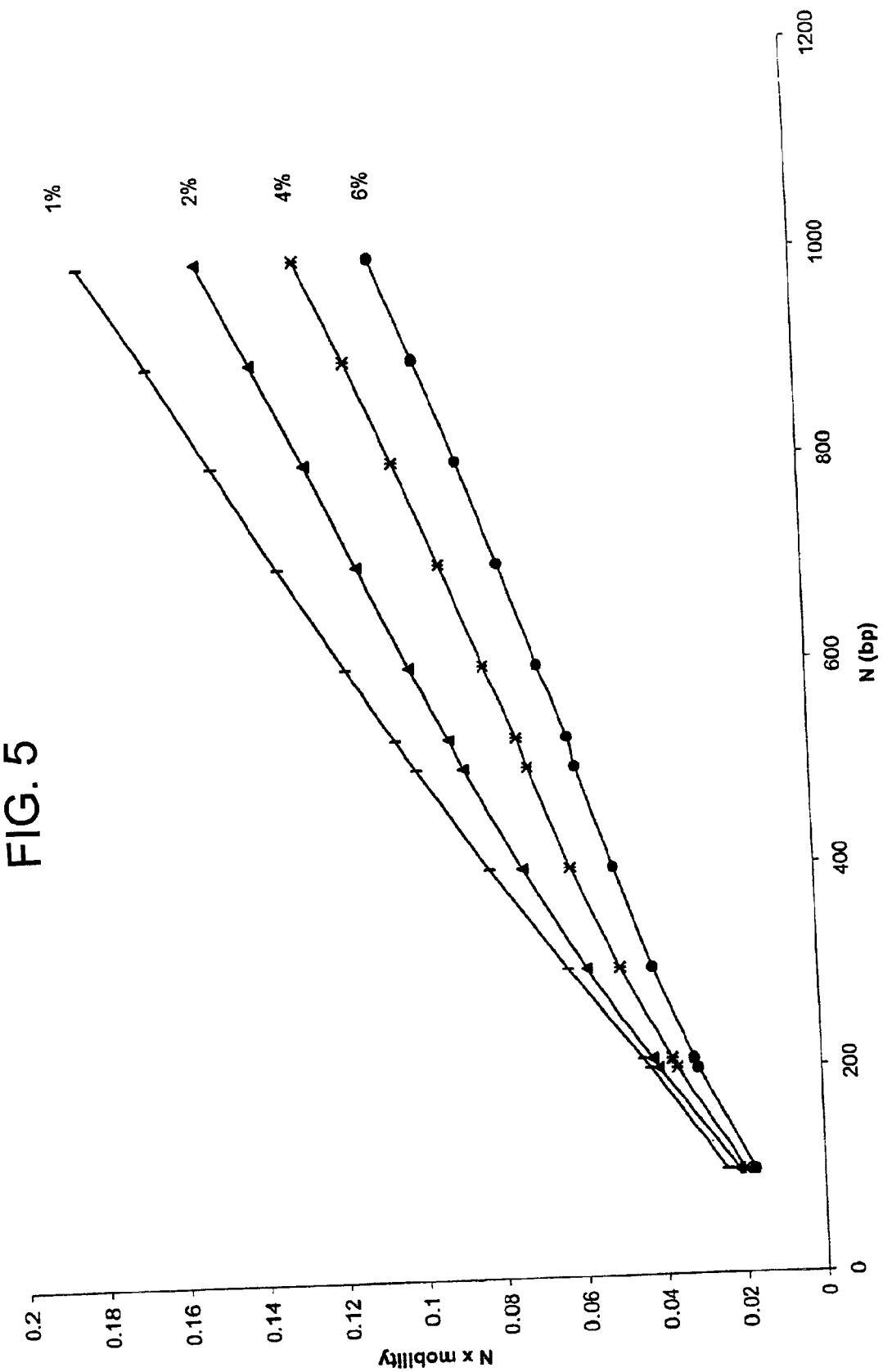
FIG. 5 are reptation plots of a 6-FAM labeled 100-bp DNA ladder in samples at various surfactant concentrations.

Reptation curves (FIG. 5) were plotted at the surfactant concentrations used in the runs, i.e., 1.4, 4 and 6%. The mobilities were independent of dye:DNA ratio up to 1:5 and field strength up to 250 V/cm. The transition from the Ogston regime to the reptation regime (loss of linearity) was less evident at 250 V/cm for the low surfactant concentrations.

Once again, at the low concentrations, the separation limit is extended.

EXAMPLE 3

This Example also shows the effect of surfactant concentration upon the separation of other fragments of DNA samples.

Test runs utilizing samples containing φX174/ HaeIII digest fragments at two different surfactant concentrations ((a) 1% $C_{16}E_6$, (b) 3% $C_{16}E_6$) were conducted (all of the conditions were as described above for Example 1).

Figure 6:
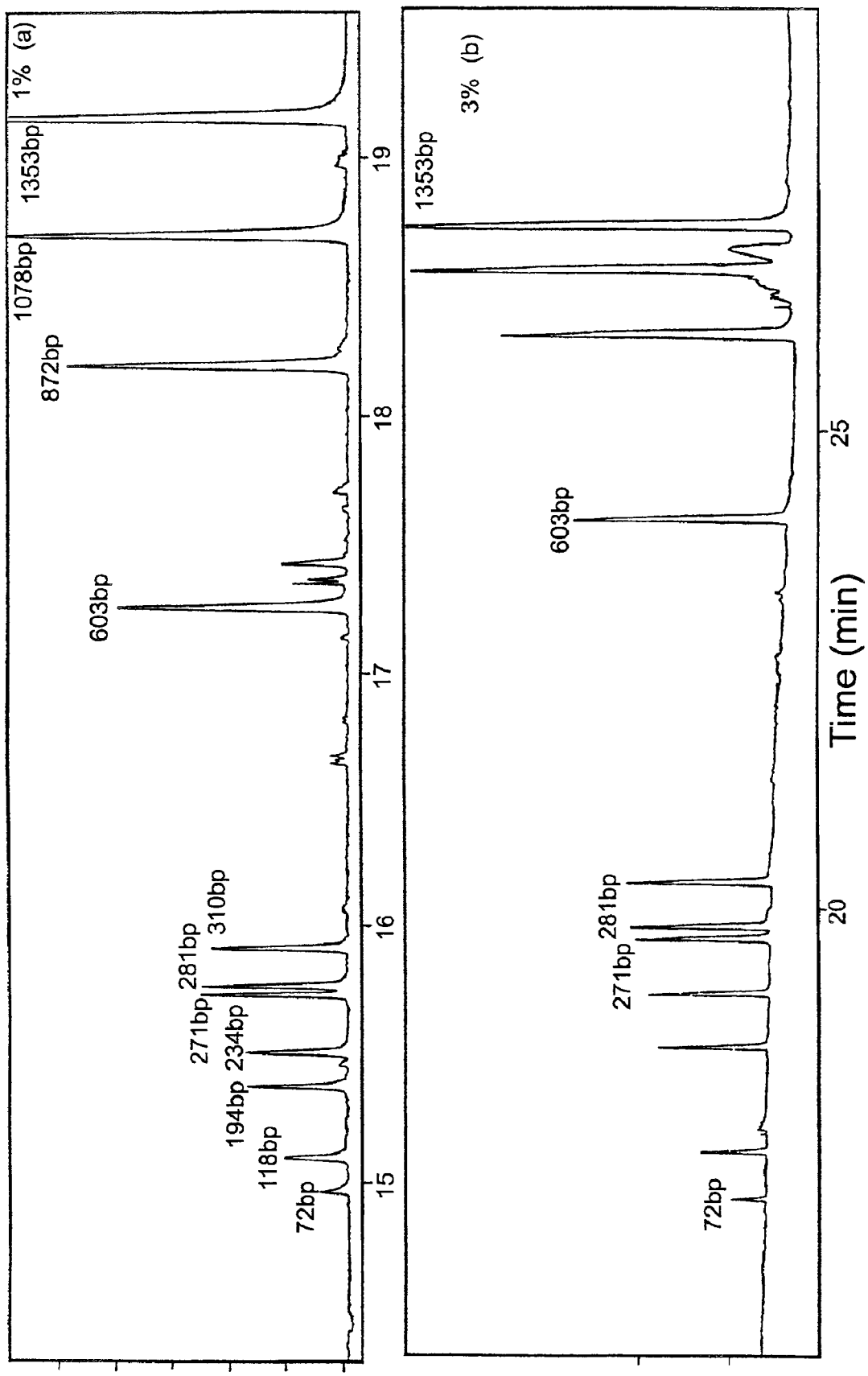
FIG. 6 are two electropherograms, labeled (a) and (b) of φX174/HaeIII digest fragments in samples separated using different surfactant concentrations.

FIGS. 6a and b show the results. The spurious peaks in FIG. 6a were due to random noise spikes in the system. The loss of resolution for large DNA and improved separation for small DNA, with an increase in the surfactant concentration is obvious, as can be seen by comparing FIGS. 6a and 6b.

EXAMPLE 4

This Example illustrates the effect of the separation temperature used upon the efficacy of the separation carried out employing the non-ionic monomeric surfactants according to the present invention.

N-alkyl polyoxyethylene ethers usually have low cloud points ($T_c$). When the temperature reaches $T_c$, micelles could not be formed (see Becher, P. *Nonionic Surfactants: Physical Chemistry*; Marcel Dekker: New York, 1967). However, $T_c$ can be adjusted by adding urea (see Briganti, G.; Puvvada, S.; Blankschtein, D. *J. Phys. Chem.* 1991, 95, 8989–8995). $C_{16}E_8$ was chosen as the sieving medium here due to the relatively high cloud point, so that a wide temperature range could be employed.

A set of test runs was conducted using samples containing 10-bp DNA ladders as markers, with each test run attempting to resolve the 10-bp ladders at a different surfactant temperature (conditions: $L_{eff}$=50 cm, 7% $C_{16}E_8$ with 1:10,000 diluted SYBR® Gold nucleic acid stain, 100 mM HEPES-TEA buffer (pH 7.0) with 3 M urea, E=200 V/cm). Again, sample introduction, as well as the surfactant introduction prior to the sample introduction, was accomplished by pressure injection as disclosed in U.S. Pat. No. 5,741,411.

Figure 7:
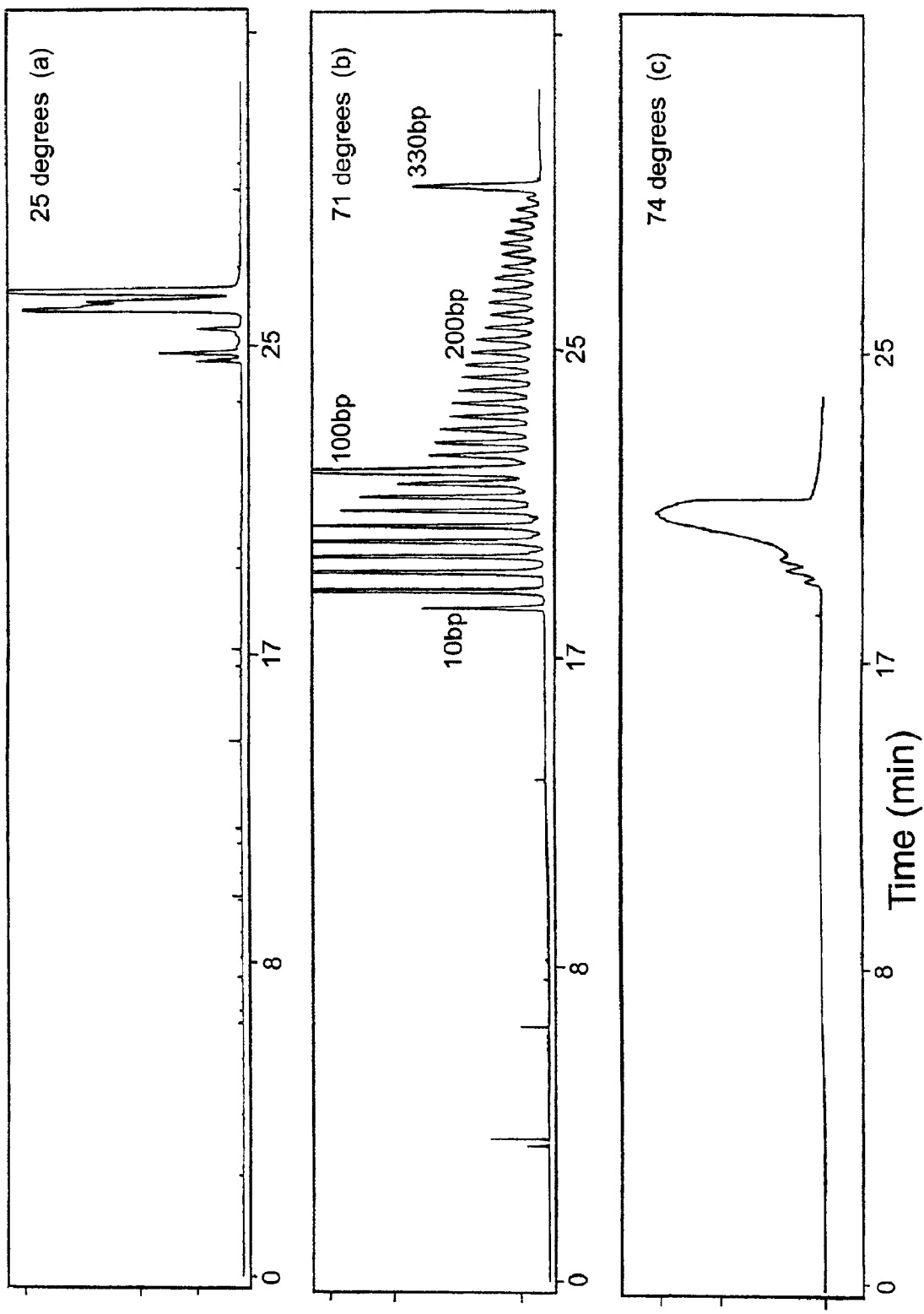
FIG. 7 are electropherograms, labeled (a)–(c), of samples including a 10-bp DNA ladder separated using non-ionic monomeric surfactant at different temperatures.

FIGS. 7a–c are electropherograms illustrating the effect of varying temperatures on the separation of the test samples including the 10-bp DNA ladders. At room temperature (i.e., 25° C.), the resolution is poor. When the temperature rises to 54° C., improved resolution is observed (data not shown). The best separation was achieved at 71° C. (FIG. 6b). When the temperature at which the separation was carried out was further increased to 74° C., the resolution is lost again, as shown in FIG. 7c. This phenomenon can be explained by the various micellar structures at different temperatures. At low temperatures, the aggregation number (hence the micellar molecular weight) for $C_{16}E_8$ is too small to form an effective network, even when the concentration is much higher than the CMC. With increasing temperature, the micelles become larger and larger until they entangle one another. Sieving separation is thus possible. When the temperature reaches its cloud point, phase separation occurs. As a result, the surfactant solution loses its ability to separate DNA fragments because of the absence of dynamic long chains of micelles in solution.

EXAMPLE 5

This Example illustrates DNA sequencing using the method of the present invention.

Figure 8:
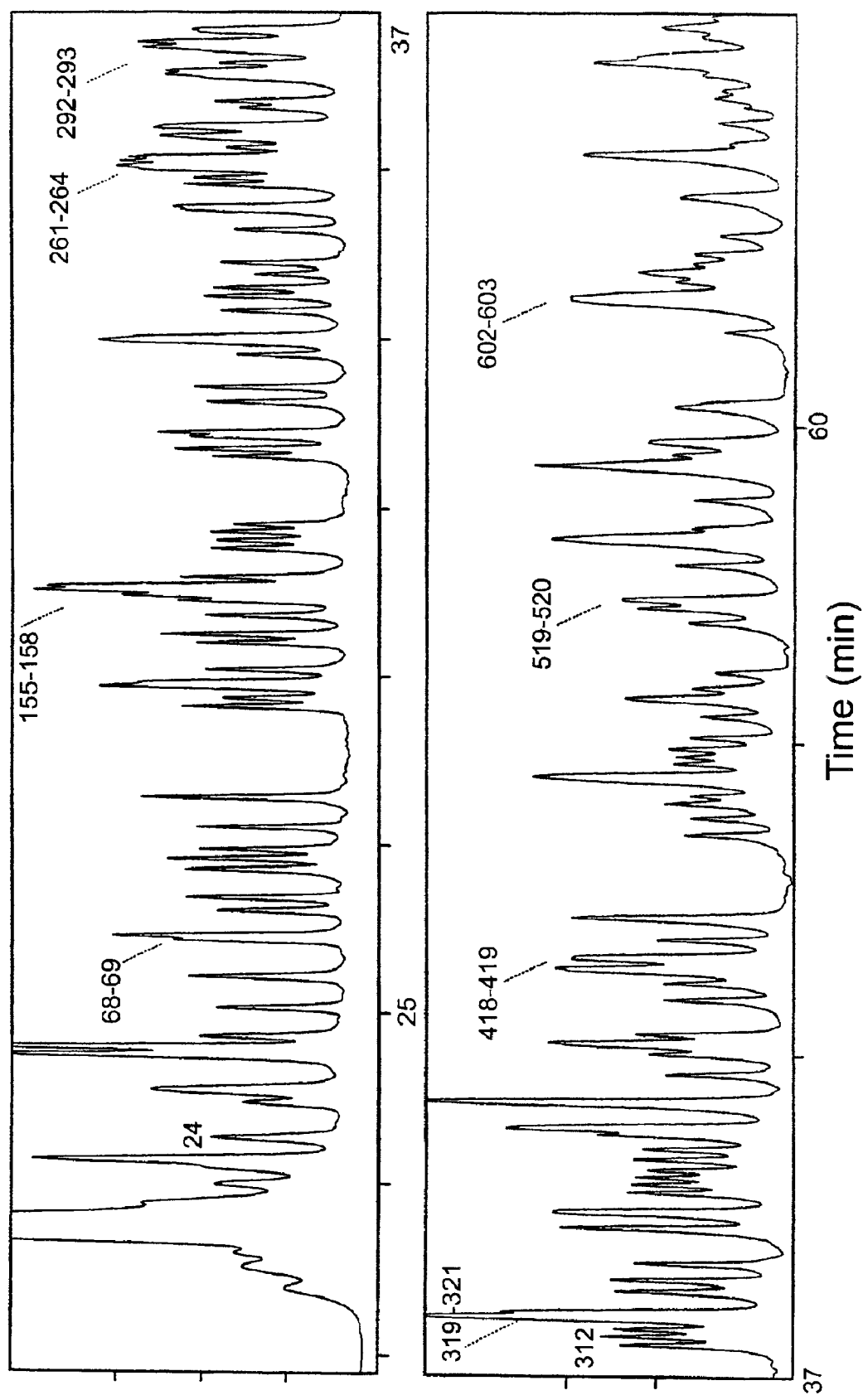
FIG. 8 is an electropherogram and showing a single-base resolution from 0.5 up to 600 bp in DNA sequencing.

A sequencing run was conducted using a sample containing BigDye primer G-labeled only M13(-21) Sanger fragments were separated using the following conditions: $L_{eff}$=65 cm, E=150 V/cm, 10% $C_{16}E_6$ in 75 mM TAPS/75 mM histidine/50 mM Tris/2 mM EDTA (pH 8.2) with 7 M urea at 34° C.; the samples were injected at a constant electric field of 150 V/cm for 30 s. FIG. 8 shows that single-base resolution of 0.5 (the minimum required for DNA sequencing) up to 600 bp is obtained within 60 min at 34° C.

Further improvements in the maximum number of bases read may be possible through additional optimization of the separation conditions. This is because strain on the polymer network is rapidly dissipated by equilibration with the monomer units, a feature that is analogous to the favorable separation of large DNA fragments at higher temperatures (see Salas-Solano, O.; Carrilho, E.; Kotler, L.; Miller, A. W.; Goetzinger, W.; Sosic, Z.; Karger, B. L. *Anal. Chem.* 1998, 70, 3996–4003, Zhou, H.; Miller, A. W.; Sosic, Z.; Buchholz, B.; Barron, A. E.; Kotler, L.; Karger, B. L. *Anal. Chem.* 2000, 72, 1045–1052).

Examples 6–9 utilize the present invention in DNA sequencing in a multiplexed capillary electrophoresis system employing UV/absorption-based detection:
Inroduction Capillary gel electrophoresis (CGE) has become an important technique in DNA sequencing because of its high speed, high resolution, flexibility, and possibility of building an integrated and automated system. Traditionally, in order to decipher the DNA sequence, radioactive or fluorescent labeling of the DNA fragments created by Sanger's chain termination reaction (see F. Sanger, S. Nicklen, A. R. Coulson, *Proc. Natl. Acad. Sci.* (*USA*), 74 (1977) 5463) is required for applying standard detection methods. Since autoradiography is labor intensive and can pose safety concerns, laser-induced fluorescence (LIF) has replaced it as the main detection method in DNA analysis. Compared to LIF, UV absorption detection is not as sensitive, but the instrumental setup is simpler and less expensive. It is easier to operate and maintain because of the use of a UV lamp rather than a laser system. No dye-label is required when using UV absorption detection in DNA analysis, since DNA has strong absorption at 254 nm. A 100-bp DNA has essentially 100 absorbers per fragment. Finally, mobility shift should not be a problem because no labels are present.

Because there are no dye labels, the DNA products from the four individual termination reactions must be run with four different capillaries in order to assemble the sequence. This is analogous to radioactive labeling and infrared single-label sequencing in slab-gel sequencing. The use of four separate capillaries at a time means that a multiplexed capillary system is likely required to achieve high-speed, high-efficiency, and high-throughput DNA sequencing. A novel absorption detection method has been applied to multiplexed capillary electrophoresis (see X. Gong, E. S. Yeung, Anal. Chem., 71 (1999) 4989). The system has proven to be very reliable and efficient in many applications, such as screening of enzyme activity, peptide mapping of proteins and genetic typing (see X. Gong, E. S. Yeung, J. Chromatogr. B, 741 (2000) 15, S. H. Kang, X. Gong, E. S. Yeung, Anal. Chem., 72 (2000) 3014, Menchen, S. M.; Johnson, B.; Winnik, M. A.; Xu, B. Electrophoresis 1996, 6, 23–28). It is shown herein that this same instrumentation can be used in DNA sequencing, employing the novel dynamic sieving matrix of the present invention, based on the self-assembly of monomeric surfactants into large aggregates under certain conditions.

Chemicals

All chemicals for preparing running buffer solutions were from Sigma (St. Louis, Mo.). The running buffer solution contained 89 mM Tris, 50 mM TAPS, 20 mM histidine, 2 mM EDTA and 7 M urea in deionized water and was filtered with a 0.22 $\mu$m cellulose membrane filter from Corning (Corning, N.Y.). The chemicals for cycle-sequencing buffer ($MgCl_2$ and Tris) were from Fisher (Fair Lawn, N.J.). 10-bp DNA ladder was obtained from Life Technologies (Frederick, Md.). The internal standards, 40-bp and 80-bp fragments, and selected cycle-sequencing primers, were prepared at the Nucleic Acid Facility (Iowa State University, Ames, Iowa). The 323-bp template was prepared using reagents in PCR Core System II from Promega (Madison, Wis.) and its Positive Control PCR Protocol. The PCR product was purified using QIAquick PCR Purification Kit from Qiagen (Valencia, Calif.). ThermoSequenase (32 U/$\mu$l), dNTPs (100 mM) and ddNTPs (10 mM) were obtained from USB/Amersham Life Sciences (Arlington Heights, Ill.).

Sequencing Reaction

In order to generate enough quantities of sequencing fragments for UV detection, the cycle-sequencing protocol introduced by Cohen et al. was used (see Froim, C. E. Hopkins, A. Belenky, A. S. Cohen, Nucl. Acids Res., 25 (1997) 4219). The reaction mixtures were combined in a microcentrifuge tube and put on ice: 200 pmol primer, 0.2 pmol template, 10 $\mu$l Tris pH 9 (250 mM), 10 $\mu$l $MgCl_2$ (50 mM), 10 $\mu$l dNTP mix (10 mM) and 32 U ThermoSequenase. Autoclaved and deionized water was added to obtain a total volume of 90 $\mu$l. 20 $\mu$l reaction mixture was added to each of the four 0.2 ml PCR reaction tubes (Molecular BioProducts, San Diego, Calif.) containing 1.25 $\mu$l of the appropriate ddNTP (1 mM). The samples were kept on ice before put onto the preheated block (95° C.) of GeneAmp PCR System 9700 (Applied Biosystems, Foster City, Calif.). The total cycle number is 200. Each cycle contains three consecutive steps: 95° C., 30 s; 52° C., 30 s; 72° C., 30 s. The product of cycle-sequencing reaction was purified by a spin column (Princeton Separation, Adelphia, N.J.), and dried in vacuum. Before injection, the DNA samples were dissolved in 3 $\mu$l deionized water and transferred to a 96-well 0.2 ml micro-tube plate (Marsh Biomedical Products, Rochester, N.Y.), spiked with 10 pmol internal standards (40-bp and 80-bp DNA fragments). After heating the plate at 95° C. for 3 min for denaturing, the sample plate was put onto ice for injection.

DNA Separation

The sieving matrix was prepared by dissolving polyoxyethylene(6) cetyl ether (Sigma) in the running buffer while gently heating and stirring. Then, the low viscosity gel was forced into a 24-capillary array from the ground end. Before injection, the matrix-filled capillary array was pre-run for 5 min at 32° C. Injection was performed at 2 kV for 2.5 min. During the run, the temperature was kept at 32° C. The running voltage of 8.8 kV was applied by a power supply from Glassman High Voltage, Inc. (Whitehorse Station, N.J.). After each run, the capillaries were regenerated by washing with 0.1 M hydrochloric acid for a few minutes, then rinsed with deionized water for half an hour.

Principles of Normalization

Even though typically in a capillary array system all the capillaries are run under exactly the same conditions (voltage, temperature, injection time and buffer pH), the surface chemistry and geometry of the capillaries are different. Also, the sieving matrix is not likely the same after being pushed or otherwise loaded into the capillaries. These variations may cause substantial variations in the migration times of DNA fragments which preclude calling bases by simply overlapping the four individual electropherograms. It has already been demonstrated that the use of two internal standards provides normalization of migration times in micellar electrokinetic chromatography (MEKC) and in capillary zone electrophoresis (CZE) (see G. Xue, H. -M. Pang, E. S. Yeung, Anal. Chem., 71 (1999) 2642). This normalization method should also be useful in unlabeled DNA sequencing. Without labeling dyes, there should be no mobility shift among the Sanger fragments. Also, since sufficient denaturant (7 M urea) has been included in the buffer, compressions in GC-rich regions are minimized. Non-uniform migration times among different capillaries are therefore only caused by the variations mentioned above. So, two DNA fragments of known lengths were used to adjust the migration times of each capillary for base calling. Another basis that makes the internal standardization method suitable for CGE is that the relationship between migration time and base number is linear over a narrow range (see A. Belenky, D. L. Smisek, A. S. Cohen, J. Chromatogr. A, 700 (1995) 137). In entangled polymer solutions, a preferable model that describes DNA movement is "the biased reptation with fluctuations" (BRF) model (see T. Duke, J. L. Viovy, A. N. Sememov, Biopolymers, 34 (1994) 239). According to this model, for small molecules (below a critical size), the mobility of the DNA fragment $\mu$ is inversely proportional to its size, represented by base number ("reptation without orientation") (see C. Heller, Electrophoresis, 20 (1999) 1962):

$$\mu/\mu_0 \sim 1/N \tag{16}$$

where $\mu_0$ is the mobility in free solution. From the definition of electrophoretic mobility:

$$\mu = v/E = x/tE \quad (17)$$

where v is the average velocity, E is the externally applied electric field strength and x is the distance travel in time t (see A. Belenky, D. L. Smisek, A. S. Cohen, *J. Chromatogr. A,* 700 (1995) 137). Eq. (16) can thus be changed to:

$$t \sim N \quad (18)$$

Based on the migration times of the two internal standards in each capillary, linear equations of t~N for the corresponding electropherograms can be determined. Then, the migration times of the DNA fragments in every capillary can be adjusted using one capillary as the migration time standard. After the normalization process, the sequence of the DNA template can be called according to the order of the adjusted migration times. For example, there are two different equations for the electropherograms of ddATP and ddCTP termination reactions:

$$N_A = a_1 t_A + b_1 \quad (19)$$

and $$N_C = a_2 t_C + b_2 \quad (20)$$

Using Eq. (19) as the standard equation, the terms in Eq. (20) can be manipulated to give the identical value for $N_C$:

$$N_C = a_1((a_2 t_C)/a_1 - (b_1 - b_2)/a_1) + b_1 \quad (21)$$

So the migration time of the C fragments can be normalized by:

$$t_C' = (a_2/a_1) t_C - (b_1 - b_2)/a_1 \quad (22)$$

EXAMPLE 6

This Example tests the normalization principle with dsDNA using a 10-bp DNA ladder as a marker.

Figure 9:
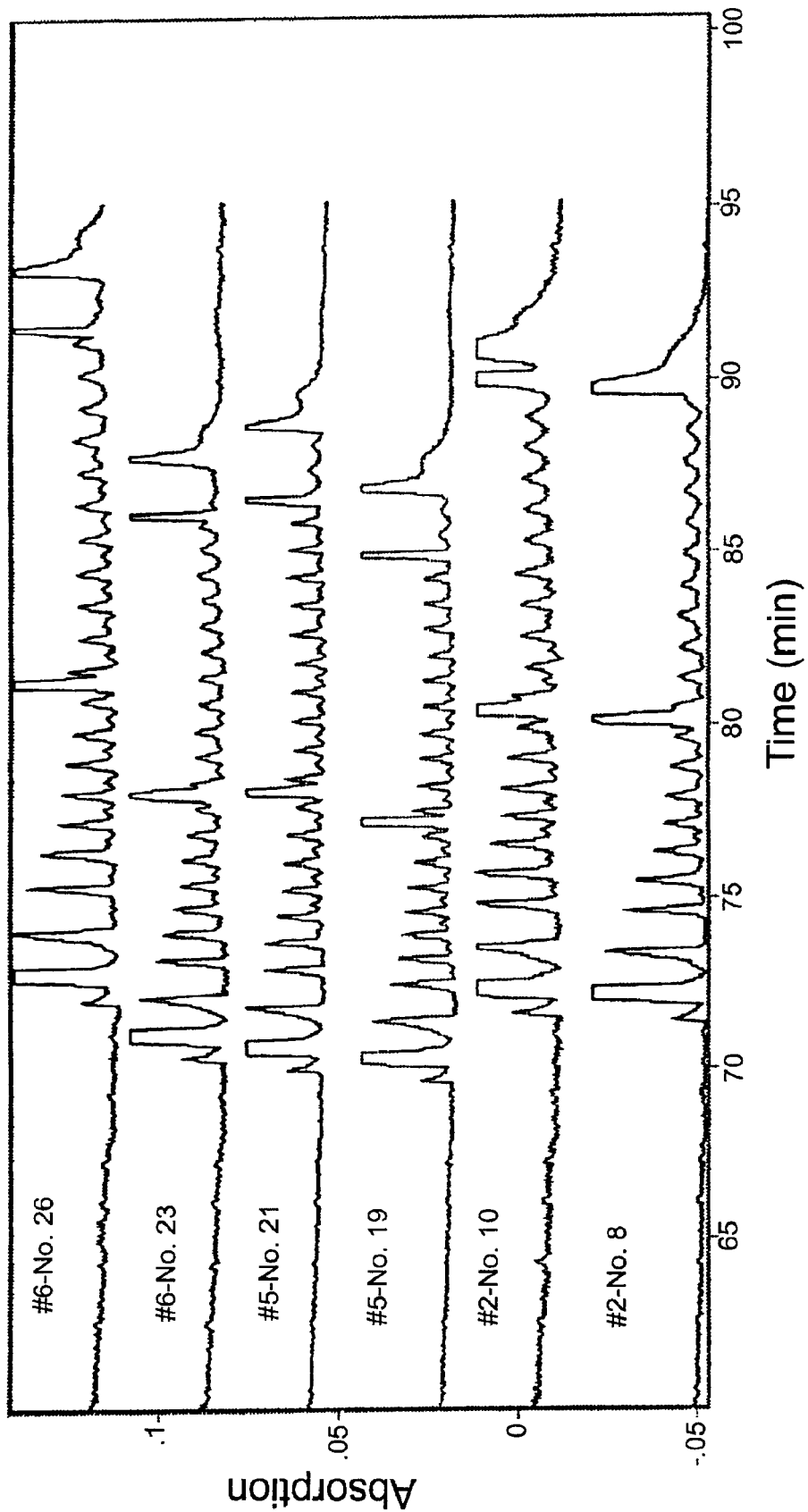
FIG. 9 is an electropherogram of a ladder separation run carried out using an UV/absorption-based detection system and employing a monomeric surfactant for size separation according to the present invention.

A sample solution containing the ladder was injected into selected capillaries containing the surfactant without dilution. The raw data is shown in FIG. 9—extracted UV electropherograms of 10-bp dsDNA ladder separation in the capillary array system. Even though the samples were the same and all the capillaries were operated under the same conditions at the same time, the migration times of the same length fragment in different capillaries are different. Here, 4 or 5 capillaries were bundled together at the ground end to facilitate filling with gel with a 100-μl glass syringe. #2, #5, and #6 indicate the group of capillaries each numbered capillary belongs to (capillaries No. 8, 10 are from bundle #2; No. 19, 21 are from bundle #5; No. 23, 26 are from bundle #6). It can be seen that the migration times in the capillaries are very different no matter whether the capillaries are from the same bundle or not.

Using the three largest peaks (10 bp, 100 bp and 330 bp) as internal standards, these electropherograms can be aligned. FIG. 10A shows the result of using 10-bp and 100-bp fragments as standards to align the other peaks. After normalization, all the peaks of the same size fragments falling in the range of 10-bp to 100-bp have the same migration times.

However, for the peaks larger than 100-bp, the 330-bp peak must be used together with the 100-bp fragment as standards to achieve the proper result (FIG. 10B). This confirms that the linear relationship only fits in a narrow range.

EXAMPLE 7

This Example illustrates the development of field strength and duration when the present invention is used in DNA sequencing.

This run used ssDNA, the Sanger fragments derived from the cycle-sequencing reaction. The four chain-termination reactions created four sets of DNA fragments, corresponding to the four bases in DNA, A, C, G, and T. In order to obtain enough signal for UV absorption detection, the dried sample was dissolved in deionized water to implement stacking in injection. A layer of silicone oil (Life Technologies, Rockville, Md.) was put on top of the vials to avoid evaporation during heating. It is known that the efficiency of CGE separation of oligonucleotides dissolved in water or other low ionic strength solvents is affected by the injection field strength and duration (see D. Demorest, R. J. Dubrow, *J. Chromatogr.,* 559 (1991) 43).

To achieve high resolution, a low injection field and a long injection time are preferably utilized (see O. Salas-Solano, M. C. Ruiz-Martinez, E. Carrilho, L. Kotler, B. L. Karger, *Anal. Chem.,* 70 (1998) 1528). It was found that a 2 kV injection voltage and a 2.5 min injection time worked best. The longer injection time did not degrade the separation performance because of stacking. This is confirmed by examining the resolution among the small DNA fragments, which would have been affected the most by electrokinetic injection.

EXAMPLE 8

Using the field strength and direction found in Example 7, this Example carries out DNA sequencing according to the present invention when employing a laboratory UV detection system.

Figure 11:
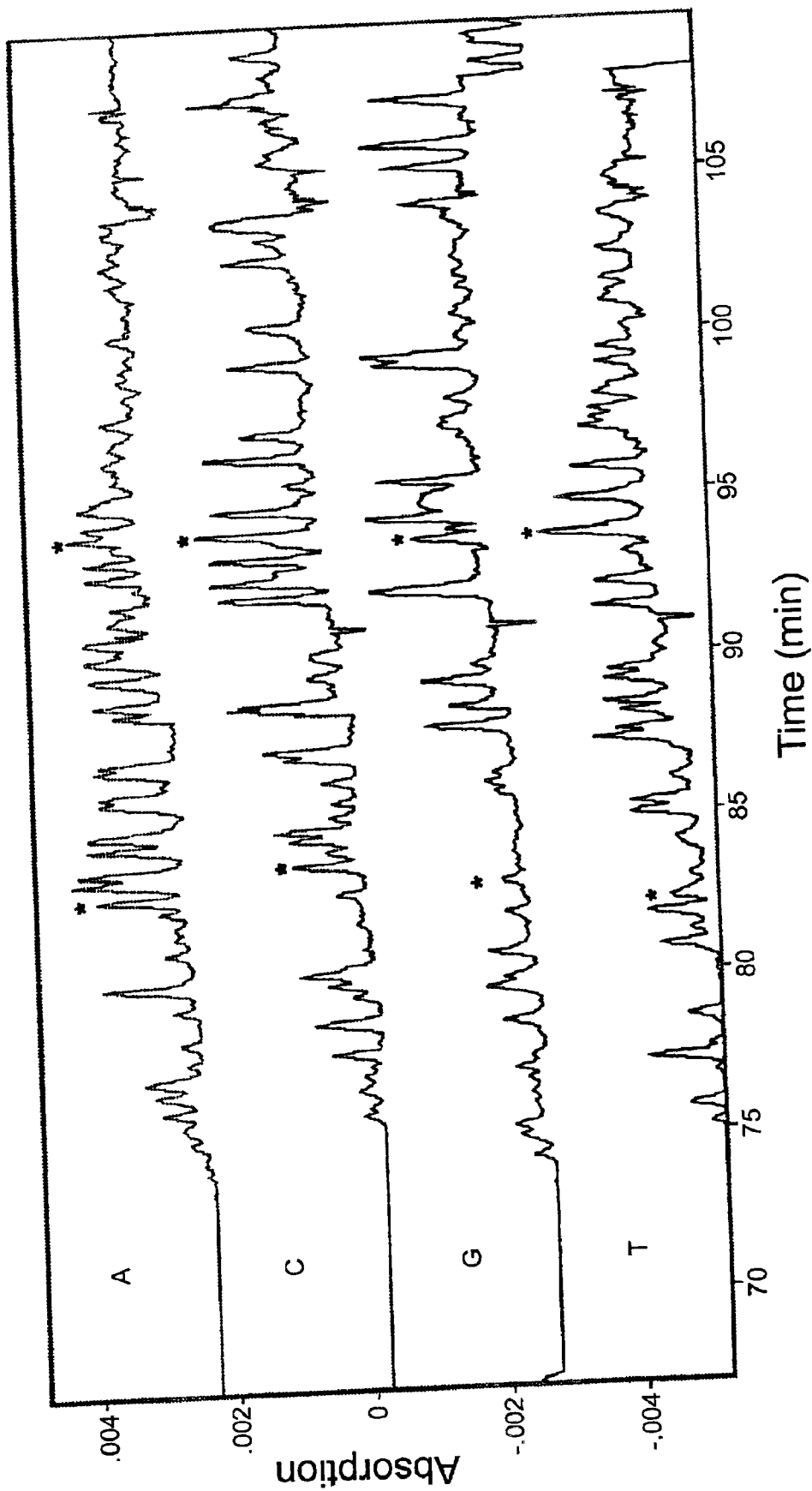
FIG. 11 are electropherograms of A, C, G, and T bases for sequencing of pGEM DNA samples using UV/absorption-based detection in a multiplexed capillary electrophoresis system according to the present invention.
Figure 12:
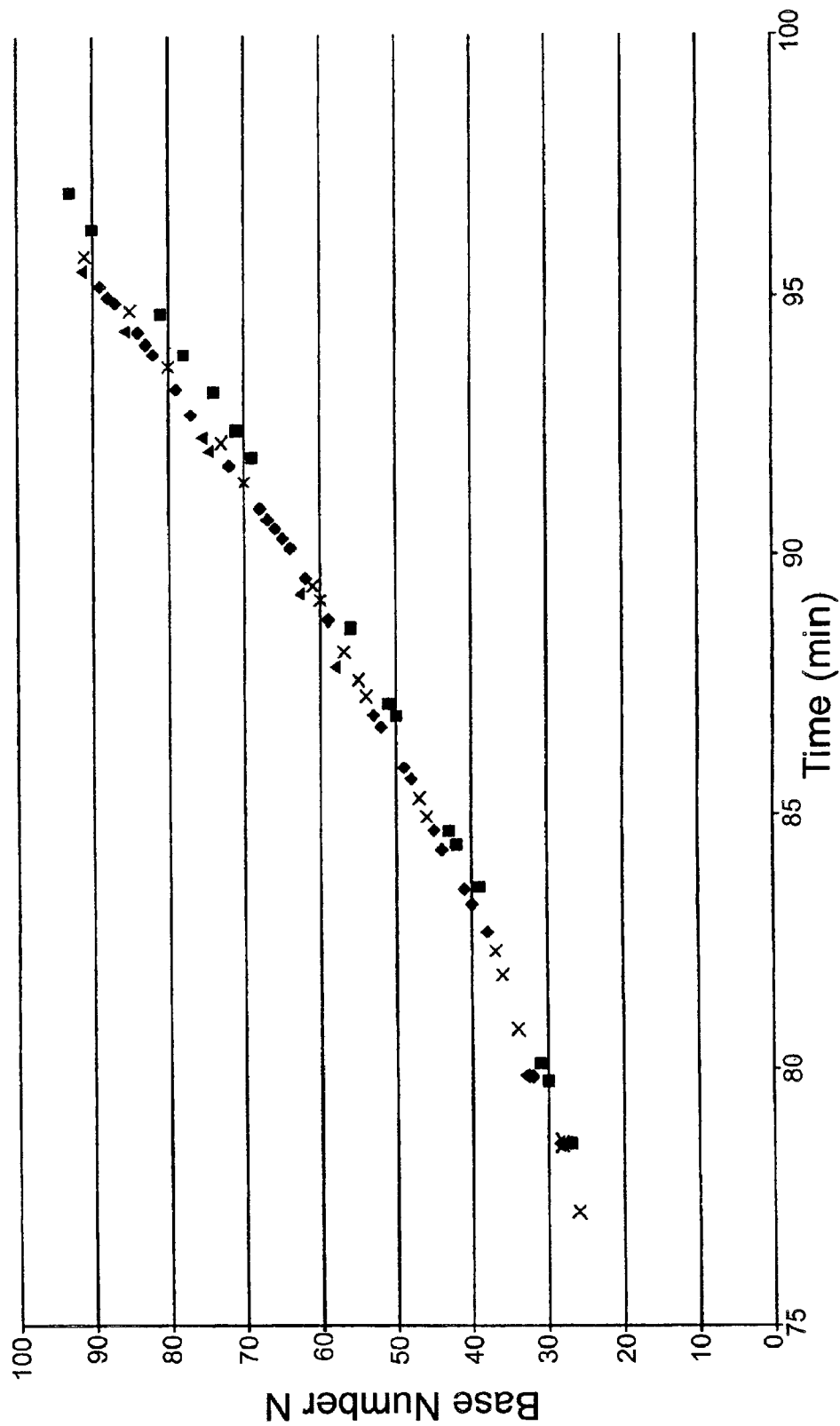
FIG. 12 is a plot of the migration times for the data depicted in FIG. 10.

Sequencing runs were conducted for pGEM DNA in four capillaries of the array. FIG. 11 shows the resulting four electropherograms for A, C, G, and T in four capillaries of the array. The known base number, N, was plotted as a function of migration time t (FIG. 12). In an individual capillary, the base number is proportional to the migration time t. However, the correct order of bases cannot be obtained from the FIG. 11 data because of migration variations among capillaries. Some fragments can be off by 5 bp.

Figure 14:
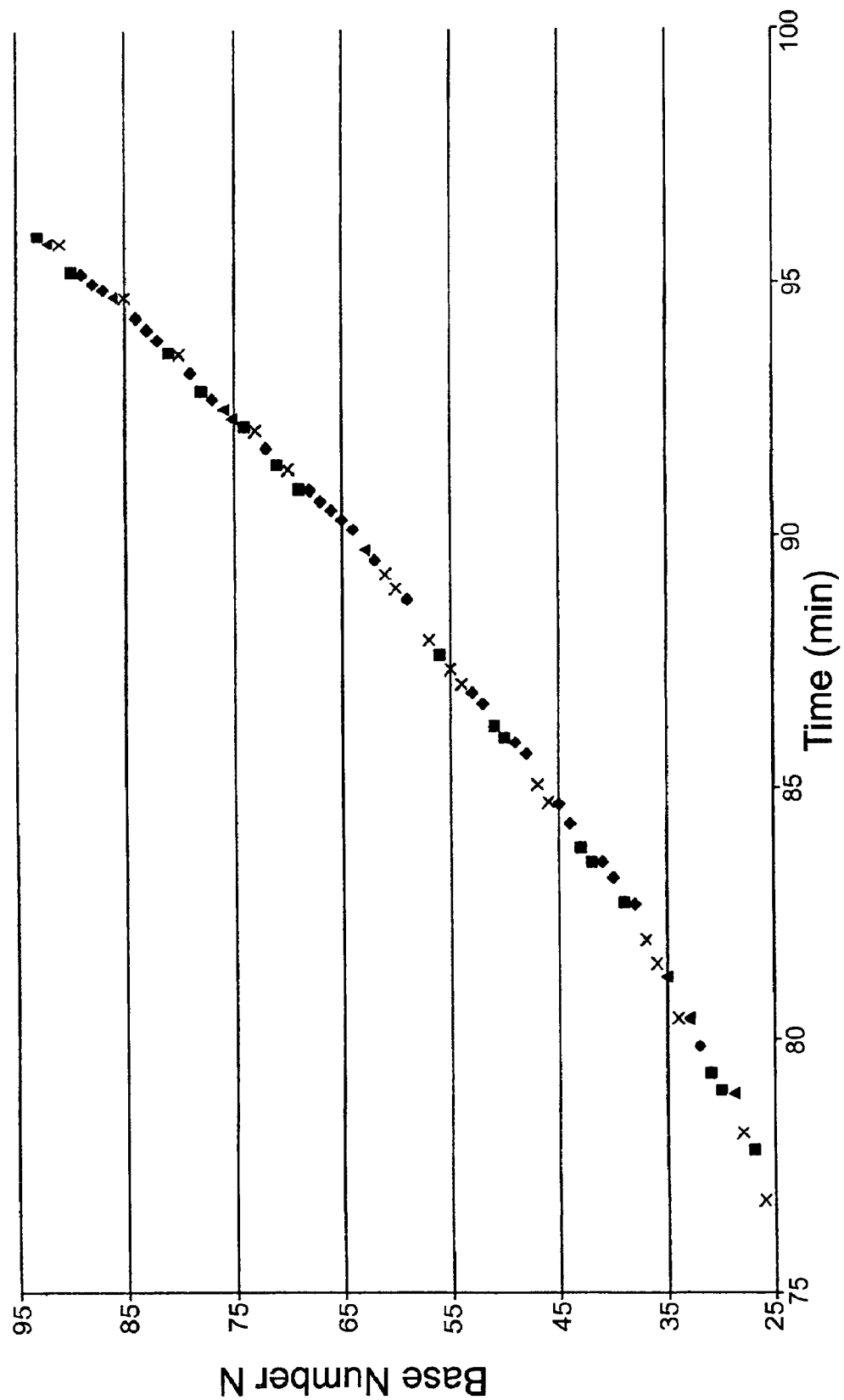
FIG. 14 is a plot similar to FIG. 11, except showing the adjusted migration times for the base numbers after normalization.

Accordingly, in these runs, two internal standards, 40-bp and 80-bp DNA fragments (the peaks with "*" on top in FIG. 11), were co-injected with the DNA samples. Based on the migration times and base number of these internal standards, all the t~N equations of the capillaries were determined. After normalization of the migration times, the four electropherograms were aligned to call the sequence of the template, as shown. FIG. 14 shows that, after normalization, all the peaks are on the same line, and the sequence can be read directly from the data in these two figures:

Table 1 sets forth the sequence:

TABLE 1

Figure 13:
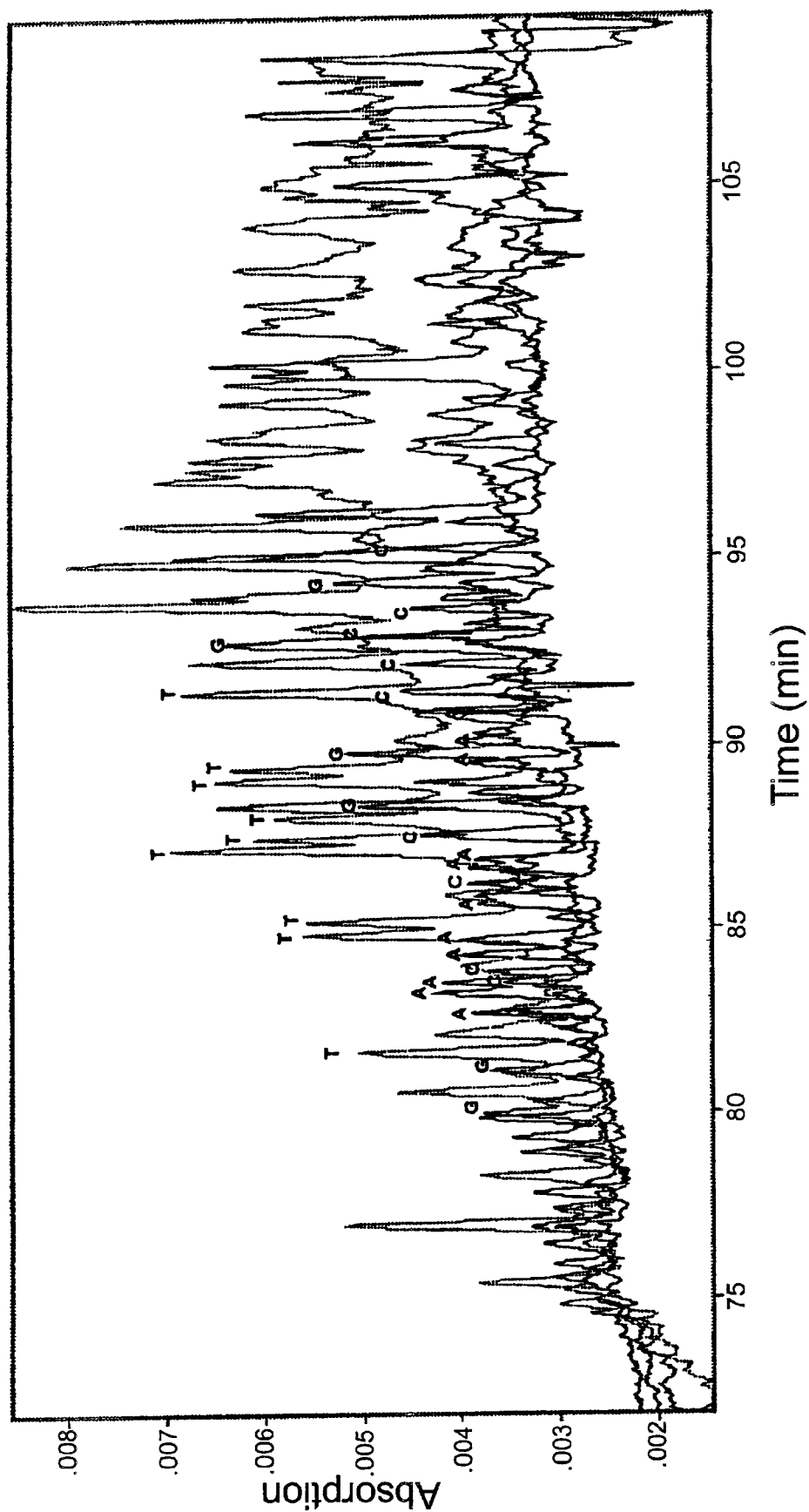
FIG. 13 is an overlay of the four electropherograms of FIG. 10 after normalization.

Adjusted migration times, the corresponding base number, and the read sequence obtained from FIGS. 13 and 14. There are no base-calling errors from 26 bp to 93 bp.

| Base No. | A (t) | C (t') | G (t') | T (t') | Sequence |
|---|---|---|---|---|---|
| 26 | | | | 23044.8 | T |
| 27 | | 23343.18 | | | C |
| 28 | | | | 23443.01 | T |
| 29 | | | 23669.29 | | G |

TABLE 1-continued

Adjusted migration times, the corresponding base number, and the read sequence obtained from FIGS. 13 and 14. There are no base-calling errors from 26 bp to 93 bp.

| Base No. | A (t) | C (t') | G (t') | T (t') | Sequence |
|---|---|---|---|---|---|
| 30 | | 23696.49 | | | C |
| 31 | | 23796.85 | | | C |
| 32 | 23957.9 | | | | A |
| 33 | | | 24130.79 | | G |
| 34 | | | | 24131.26 | T |
| 35 | | | 24376.79 | | G |
| 36 | | | | 24455.01 | T |
| 37 | | | | 24595.22 | T |
| 38 | 24804.5 | | | | A |
| 39 | | 24816.53 | | | C |
| 40 | 24963.9 | | | | A |
| 41 | 25055.5 | | | | A |
| 42 | | 25060.04 | | | C |
| 43 | | 25145.64 | | | C |
| 44 | 25288.5 | | | | A |
| 45 | 25403.5 | | | | A |
| 46 | | | | 25412.33 | T |
| 47 | | | | 25523.66 | T |
| 48 | 25704.5 | | | | A |
| 49 | 25773.5 | | | | A |
| 50 | | 25808.86 | | | C |
| 51 | | 25879.7 | | | C |
| 52 | 26009.5 | | | | A |
| 53 | 26078.5 | | | | A |
| 54 | | | | 26132.64 | T |
| 55 | | | | 26222.16 | T |
| 56 | | 26305.72 | | | C |
| 57 | | | | 26388.89 | T |
| 58 | | | 26489.61 | | G |
| 59 | 26626.5 | | | | A |
| 60 | | | | 26690.83 | T |
| 61 | | | | 26780.96 | T |
| 62 | 26864.9 | | | | A |
| 63 | | | 26898.78 | | G |
| 64 | 27040.5 | | | | A |
| 65 | 27100 | | | | A |
| 66 | 27160 | | | | A |
| 67 | 27211.5 | | | | A |
| 68 | 27275 | | | | A |
| 69 | | 27279.75 | | | C |
| 70 | | | | 27393.22 | T |
| 71 | | 27426.74 | | | C |
| 72 | 27526.9 | | | | A |
| 73 | | | | 27628.37 | T |
| 74 | | 27650.57 | | | C |
| 75 | | | 27699.77 | | G |
| 76 | | | 27765.24 | | G |
| 77 | 27816.9 | | | | A |
| 78 | | 27865.05 | | | C |
| 79 | 27969.7 | | | | A |
| 80 | | | | 28082.4 | T |
| 81 | | 28094.3 | | | C |
| 82 | 28169.4 | | | | A |
| 83 | 28230 | | | | A |
| 84 | 28295.9 | | | | A |
| 85 | | | | 28414.95 | T |
| 86 | | | 28423.98 | | G |
| 87 | 28466.5 | | | | A |
| 88 | 28502 | | | | A |
| 89 | 28562.9 | | | | A |
| 90 | | 28579.84 | | | C |
| 91 | | | | 28738.19 | T |
| 92 | | | 28756.18 | | G |
| 93 | | 28788.91 | | | C |

In the worst case, there exists only a 0.5 bp error. The standard fragments added prevent base calling at those specific locations. However, staggered sizes can be used to span a large normalization range and to recover any missing information.

The protocol used compensates for the amount of product by using short template, high concentration of primer, and high number of reaction cycles. So, the read length is short in this experiment. Especially for the A reaction, no peaks can be seen in the electropherogram after 89 bp. For the C, G, T reactions, even though the read length was up to 150 bp, the right sequence can only be called from 26 bp to 93 bp because of the limited useful range of two internal standards. Clearly, such short sequences may well not allow the present scheme to compete with current instrumentation for genomic sequencing. However, for diagnosis (see X. Gong, E. S. Yeung, J. Chromatogr. B, 741 (2000) 15) or antisense characterization (see A. Belenky, D. L. Smisek, A. S. Cohen, J. Chromatogr. A, 700 (1995) 137), read lengths of 100 bp are adequate. The present scheme therefore offers an alternative to mass spectrometric analysis of short fragments (see Z. Fei, T. Ono, L. M. Smith, Nucl. Acids Res., 26 (1998) 2827). The fact that capillary arrays are eventually scalable to 384 or even 1536 formats means that using 4 lanes at a time is not unreasonable. The unusually large number of amplification cycles implies a longer sample preparation time. However, that is preferably performed off-line in an automated system and has little effect on the throughput.

EXAMPLE 9

This Example illustrates that data obtained from different capillaries using the present invention after normalization can be compared.

Figure 15:
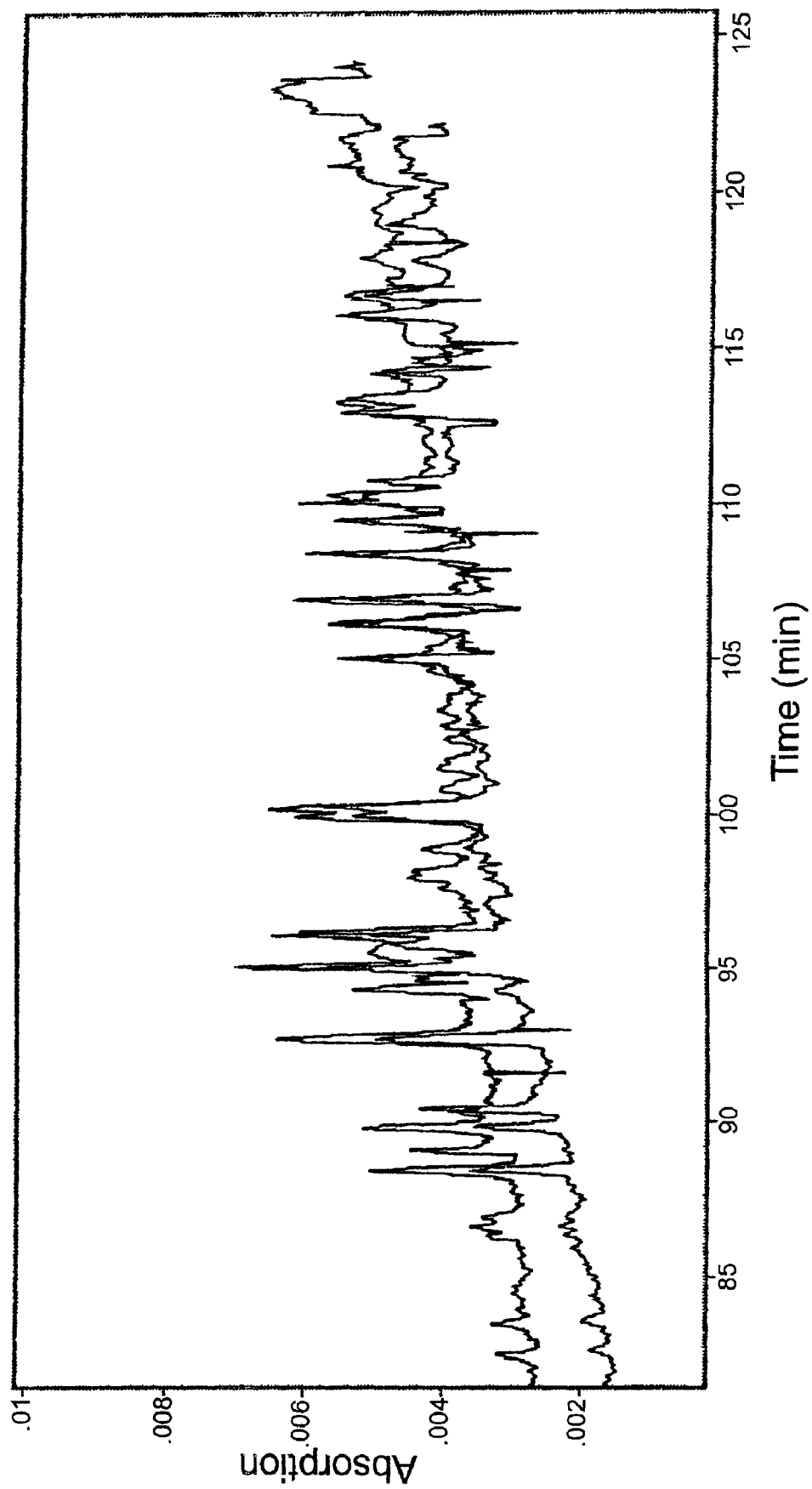
FIG. 15 is an overlay of two electropherograms after normalization and illustrating the peaks from two different capillaries aligned for the G bases.

FIG. 15 shows the result of overlaying two electropherograms of two G bases from different capillaries after normalization. A separate G sample was run with the other four A, C, G, T sample run (Example 8 and FIG. 14) in the same array. After migration time correction, the peaks for the same length fragments were aligned exactly. It was thus confirmed that, after migration time correction, there is no mobility shift among the capillaries. Some small ghost peaks (the peaks without matching peaks in the other electropherogram) were found which only showed up in one of the electropherograms, presumably due to the loss of fidelity of the cycle-sequencing reaction.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of carrying out the size separation in a sample having at least one target analyte which comprises:
   (a) providing the sample solution having target analyte(s),
   (b) providing a sieving medium in a receptacle for such medium comprising a non-ionic monomeric surfactant of the general formula, B-A, wherein A is a hydrophilic moiety and B is a hydrophobic moiety, present in a solvent at a concentration forming a self-assembled micelle configuration under selected conditions and having an aggregation number providing an equivalent weight capable of effecting the size separation of the sample solution so as to resolve the target analyte(s), and
   (c) subjecting the sample solution to the sieving medium to carry out the size separation.

2. The method of claim 1 wherein the non-ionic monomeric surfactant is an n-alkyl polyoxyethylene ether.

3. The method of claim 1 wherein the aggregation number is at least 100.

4. The method of claim 3 wherein the aggregation number is at least about 1,000.

5. The method of claim 3 wherein the aggregation number is at least about 10,000.

6. The method of claim 1 wherein the temperature of the solvent containing the non-ionic monomeric surfactant and the sample solution is increased or decreased in order to adjust the aggregation number prior to carrying out the size separation.

7. The method of claim 1 wherein the concentration of the non-ionic monomeric surfactant is adjusted to provide the micelle configuration capable of effecting size separation.

8. The method of claim 1 wherein a denaturant is added to the solvent containing a non-ionic monomeric surfactant in order to adjust the aggregation number.

9. The method of claim 2 wherein the n-alkyl polyoxyethylene ether is a member selected from the group consisting of hexaethylene glycol monotetradecyl ether, hexaethylene glycol monohexadecyl ether, and octaethylene glycol monohexadecyl ether.

10. The method of claim 1 wherein the sieving medium receptacle is at least one capillary tube and the separation is carried out using capillary electrophoresis.

11. The method of claim 10 wherein there are a plurality of capillary tubes.

12. The method of claim 1 wherein the solvent is water.

13. A system for the size separation and detection of target analyte(s) in a sample having at least one target analyte, comprising:
   (a) at least one receptacle for the separation of said target analyte(s) in said sample having an inlet and an outlet and comprising a sieving medium comprising a non-ionic monomeric surfactant of the general formula, B-A, wherein A is a hydrophilic moiety and B is a hydrophobic moiety, present in a solvent at a concentration forming a self-assembled micelle configuration under selected conditions and having an aggregation number providing an equivalent weight capable of effecting the size separation of the constituents of the sample solution so as to resolve the target analyte(s);
   (b) a sample introduction means for introducing the sample solution into the receptacle and causing size separation as the target analyte(s) moves through the receptacle outlet; and
   (c) means for detecting the target analyte(s).

14. The system of claim 13 wherein said non-ionic monomeric surfactant is an n-alkyl polyoxyethylene ether.

15. The system of claim 14, wherein said n-alkyl polyoxyethylene ether is a member selected from the group consisting of hexaethylene glycol monotetradecyl ether, hexaethylene glycol monohexadecyl ether, and octaethylene glycol monohexadecyl ether.

16. The system of claim 13, wherein said means for detection of said target analyte(s) is by laser-induced fluorescence.

17. The system of claim 13, wherein said means for detection of said target analyte(s) is by UV absorption detection.

18. The system of claim 13, wherein said receptacle is a capillary tube.

19. The system of claim 13, wherein the system comprises a plurality of receptacles.

20. The system of claim 19, wherein said receptacles are capillaries and the separation is carried out by multiplexed capillary electrophoresis.

21. A method of detecting at least one target analyte in a sample which comprises:
   (a) providing the sample solution having the target analyte(s),
   (b) providing at least one receptacle, said receptacle(s) having an inlet and an outlet;
   (c) providing a sieving medium comprising a non-ionic monomeric surfactant of the general formula, B-A, wherein A is a hydrophilic moiety and B is a hydrophobic moiety, present in a solvent and forming a self-assembled micelle configuration under selected conditions and having an aggregation number (n) providing an equivalent weight capable of effecting the size separation so as to resolve the target analyte(s), the sieving medium not forming a micelle capable of effecting the size separation in a first temperature range, but forming a micelle capable of effecting the size separation at a second temperature range;
   (d) introducing said sieving medium into the receptacle at a temperature within the first temperature range;
   (e) adjusting the temperature of said sieving medium within said receptacle(s) to a temperature within said second temperature range;
   (f) introducing said sample solution into the inlet of said receptacle to effect size separation; and
   (g) detecting the target analyte(s).

22. The method of claim 21 wherein the non-ionic monomeric surfactant is a n-alkyl polyoxyethylene ether.

23. The method of claim 21, wherein said receptacle is a capillary.

24. The method of claim 21, wherein a plurality of receptacles are provided for carrying out said separation.

25. The method of claim 24, wherein said receptacles are capillary tubes.

26. A electrophoresis system for the separation and detection of analyte(s) in a sample solution containing at least one analyte, comprising:
(1) at least one receptacle for the separation of said analyte(s), said receptacle having an inlet and an outlet,
(2) a sieving medium within said receptacle comprising a non-ionic monomeric surfactant of the general formula, B-A, wherein A is a hydrophilic moiety and B is a hydrophobic moiety, present in a solvent and forming a self-assembled micelle configuration under selected conditions and having an aggregation number providing an equivalent weight capable of effecting the size separation so as to resolve the target analyte(s) of said sample solution, the sieving medium not forming a micelle capable of effecting the size separation in a first temperature range, but forming a micelle capable of effecting the size separation at a second temperature range;
(3) means for introducing said sieving medium into the receptacle at a temperature within the first temperature range;
(4) means for adjusting the temperature of said sieving medium within said receptacle to a temperature within said second temperature range;
(5) means for introducing said sample solution containing said analyte(s) into said receptacle containing said sieving medium for separation; and
(6) means for detecting said analyte(s).

27. The electrophoresis system of claim 26 wherein the non-ionic monomeric surfactant is an n-alkyl polyoxyethylene ether.

28. The electrophoresis system of claim 26, wherein the receptacle is a capillary tube.

29. The electrophoresis system of claim 26, wherein the system comprises a plurality of receptacles for carrying out said separation.

30. The electrophoresis system of claim 29, wherein said receptacles are capillary tubes.

31. The electrophoresis system of claim 26, wherein the means for detecting said analyte(s) is by laser-induced fluorescence.

32. The electrophoresis system of claim 26, wherein the means for detecting said analyte(s) is by UV/absorption detection.

* * * * *

UNITED STATES PATENT AND TRADEMARK OFFICE
CERTIFICATE OF CORRECTION

PATENT NO. : 6,878,254 B2
DATED : April 12, 2005
INVENTOR(S) : Edward S. Yeung et al.

It is certified that error appears in the above-identified patent and that said Letters Patent is hereby corrected as shown below:

Column 22,
Line 9, "(b) a sample introduction means for introducing the" should read -- (b) sample introduction means for introducing the --.
Line 37, "(s)," should read -- (s); --.

Signed and Sealed this

Sixth Day of September, 2005

JON W. DUDAS
*Director of the United States Patent and Trademark Office*